(12) United States Patent
Sumi et al.

(10) Patent No.: US 7,177,011 B2
(45) Date of Patent: Feb. 13, 2007

(54) IMAGE DRAWING APPARATUS AND IMAGE DRAWING METHOD

(75) Inventors: Katsuto Sumi, Kanagawa-ken (JP); Takayuki Uemura, Kanagawa-ken (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 48 days.

(21) Appl. No.: 11/154,711

(22) Filed: Jun. 17, 2005

(65) Prior Publication Data

US 2005/0280793 A1    Dec. 22, 2005

(30) Foreign Application Priority Data

Jun. 17, 2004    (JP)    ............................. 2004-179587

(51) Int. Cl.
  G03B 27/54    (2006.01)
  B41J 2/455    (2006.01)
  B41J 15/14    (2006.01)
(52) U.S. Cl. .................... 355/67; 347/233; 347/241
(58) Field of Classification Search ................ 355/53, 355/67; 347/233, 234, 235, 241, 243
See application file for complete search history.

(56) References Cited

U.S. PATENT DOCUMENTS 6,244,702 B1 * 6/2001 Sakino et al. ............... 347/106

FOREIGN PATENT DOCUMENTS

| JP | 9-277571 | * 10/1997 |
| JP | 2003-195512 A | 7/2003 |
| JP | 2004-9595 A | 1/2004 |

* cited by examiner

*Primary Examiner*—Alan Mathews
(74) *Attorney, Agent, or Firm*—Sughrue Mion, PLLC

(57) ABSTRACT

In an image drawing apparatus and an image drawing method for forming a desired two-dimensional pattern on an image drawing surface by using a plurality of image drawing heads, uneven density and resolution caused by errors in relative positions of the heads and installation angles thereof and by an effect of pattern distortion can be reduced. A rectangular two-dimensional pixel array is installed in each of exposure heads in an exposure apparatus (image drawing apparatus) so as to make a predetermined angle with the direction of scanning, facing an exposure surface of a photosensitive material. Combinations of slits and photo detectors detect positions of light spots in the exposure surface comprising inter-head relay areas. Pixels in the pixel arrays are selected so as to realize N-overlay exposure ideally by causing overexposure and underexposure to be minimal in the inter-head relay areas.

13 Claims, 14 Drawing Sheets

EXPOSED AREAS

DIRECTION OF SCANNING
CONSTANT LOW SPEED AT EACH SCANNING(40mm/s)

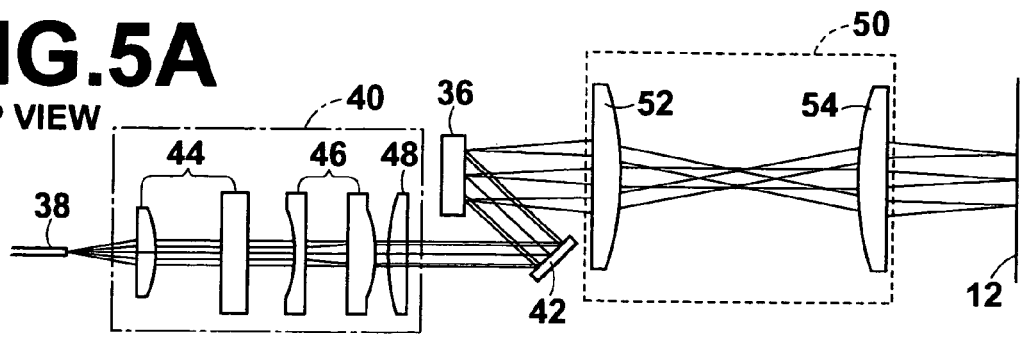
FIG.5A TOP VIEW
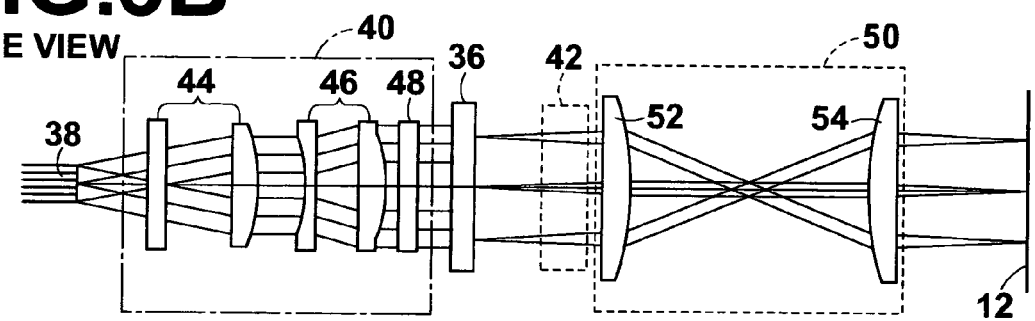
FIG.5B SIDE VIEW
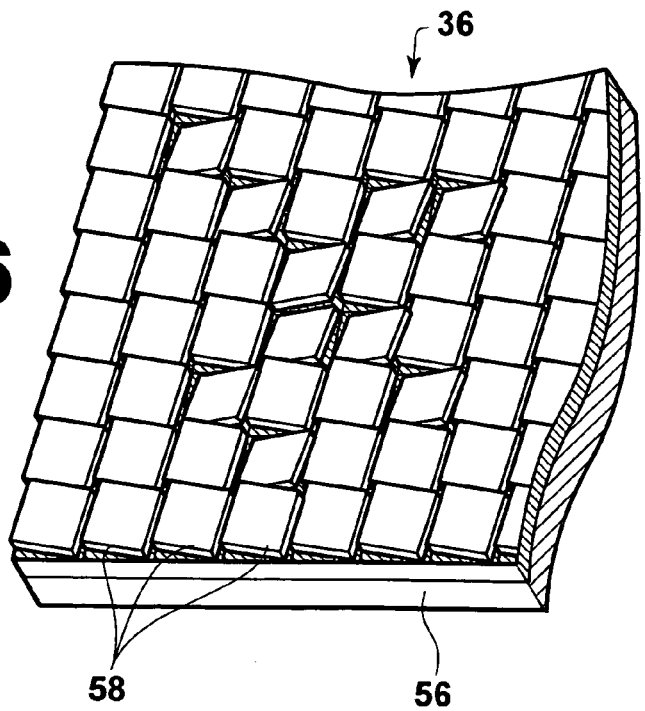
FIG.6

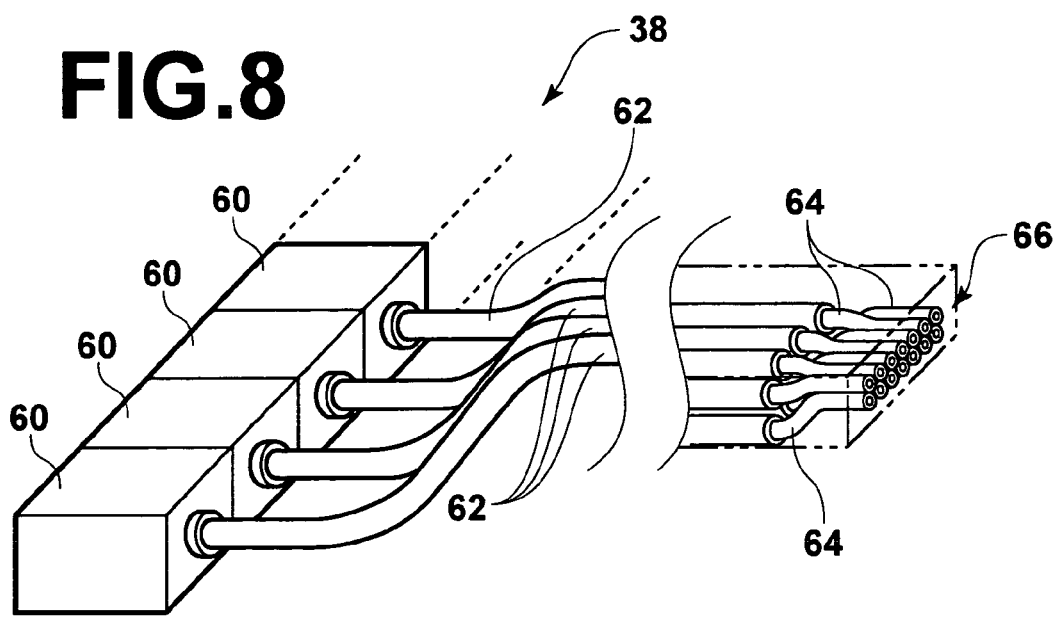
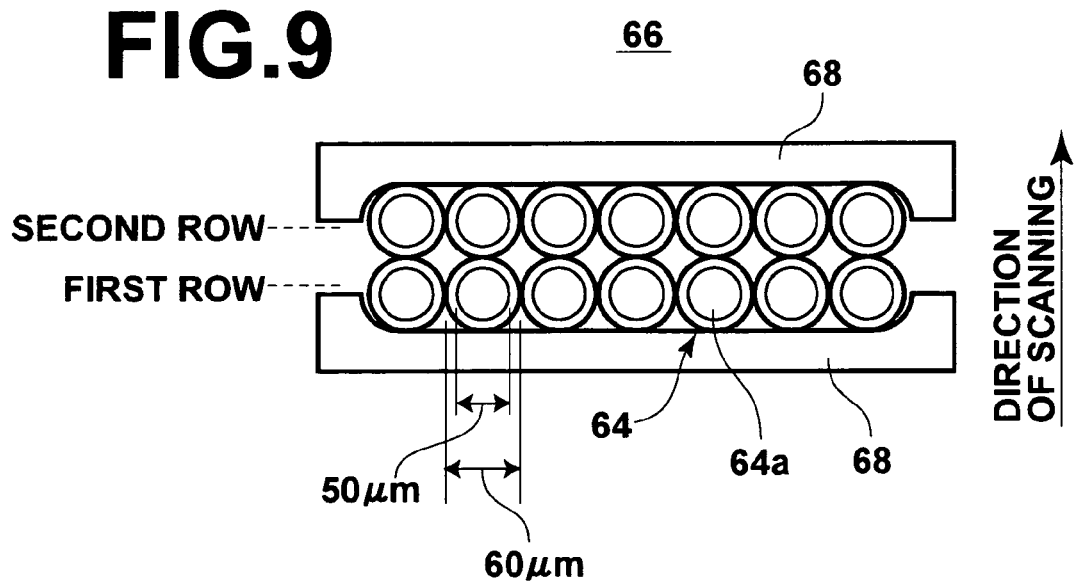

IMAGE DRAWING APPARATUS AND IMAGE DRAWING METHOD

BACKGROUND OF THE INVENTION

1. Field of the Invention

The present invention relates to an image drawing apparatus and an image drawing method. More specifically, the present invention relates to an image drawing apparatus and an image drawing method for forming a two-dimensional pattern represented by image data on an image drawing surface by using a plurality of image drawing heads.

2. Description of the Related Art

There have been known various kinds of image drawing apparatuses each comprising an image drawing head for forming a desired two-dimensional pattern represented by image data on an image drawing surface. As a representative example of such an image drawing apparatus, an exposure apparatus for forming a desired two-dimensional pattern on an exposure surface of a photosensitive material or the like by using an exposure head in order to generate a semiconductor substrate or printing plate can be listed. Such an exposure head in an exposure apparatus generally has a pixel array comprising a plurality of pixels for generating light spots forming a desired two-dimensional pattern, such as a light-source array or spatial light modulators. The desired two-dimensional pattern can be formed on an exposure surface by causing the exposure head to operate with movement relative to the surface.

In such an exposure apparatus, covering a sufficiently large exposure surface with a single exposure head is in some cases difficult for a configuration of a pixel array or the like, as in the case where a digital micro-mirror device (DMD) of a generally available size is used as spatial light modulators, for example. Therefore, an exposure apparatus using a plurality of exposure heads in parallel has been proposed. Furthermore, in order to improve resolution in the direction that is perpendicular to the direction opposite to the direction of exposure surface movement (hereinafter, the direction opposite to that of exposure surface movement is referred to as the scanning direction), an exposure apparatus using exposure heads has been proposed wherein pixel arrays having two-dimensionally arranged pixels are installed diagonally to the scanning direction.

For example, Japanese Unexamined Patent Publication No. 2004-009595 describes an exposure apparatus that includes exposure heads laid out diagonally to the scanning direction and comprises DMD's having micro-mirrors laid out in a rectangular grid shape. The exposure heads are installed in the exposure apparatus in such a manner that triangular areas formed as a result of diagonal installation of the DMD's if both ends of each of the DMD's are cut by lines parallel to the direction of scanning are complemented each other by the neighboring DMD's placed along the direction perpendicular to the scanning direction.

Furthermore, Japanese Unexamined Patent Publication No. 2003-195512 describes an exposure apparatus whose exposure areas formed by DMD's are shaped into parallelograms. In this exposure apparatus, exposure heads comprising the DMD's formed in a rectangular grid shape are placed perpendicular to or slightly diagonal to the scanning direction, and the exposure areas of the neighboring DMD's laid out in the direction perpendicular to the scanning direction overlap with a predetermined width. In areas corresponding to the overlaps of the exposure areas, the number of micro-mirrors to be driven in the DMD's is gradually increased or decreased in a predetermined proportion. In this manner, the exposure areas formed into parallelograms can be realized.

However, in the case where exposure is carried out by using exposure heads each comprising a pixel array having two-dimensionally placed pixels whose columns are placed diagonally to the scanning direction, fine adjustment of positions and angles of the heads relative to each other is generally difficult, and slight deviation from ideal positions and angles is often observed. Furthermore, distortion may be observed in a pattern actually formed on an exposure surface, due to various kinds of optical aberration between the pixel arrays and the exposure surface and distortion of the pixel arrays itself. Therefore, even in the case where an exposure apparatus is used in such a state that exposure areas formed by pixel arrays are smoothly relayed in an ideal state with no such distortion and deviation, complete elimination of such distortion and deviation is extremely difficult in practice. Consequently, uneven resolution and density do occur in areas drawn by neighboring heads (hereinafter referred to as inter-head relay areas) in the two-dimensional pattern on the exposure surface.

In order to solve this problem, improvements may be made in accuracy of fine adjustment of positions and angles between exposure heads and in adjustment of optical system. However, pursuing this accuracy swells manufacturing cost.

The same problem can also occur in an image drawing apparatus of other types, such as an inkjet printer comprising an inkjet recording head used for drawing an image by propelling droplets of ink to a surface whereon the image is drawn.

SUMMARY OF THE INVENTION

The present invention has been conceived based on consideration of the above circumstances. An object of the present invention is to reduce unevenness in resolution and density in inter-head relay areas in an actual image drawing surface, caused by an error in positions and angles between image drawing heads and by a pattern distortion or the like, in an image drawing apparatus and in an image drawing method for drawing a desired two-dimensional pattern on the image drawing surface with use of the image drawing heads.

More specifically, an image drawing apparatus of the present invention is an apparatus for forming a two-dimensional pattern represented by image data on an image drawing surface by "N-overlay image drawing" (where N refers to a natural number), and the image drawing apparatus comprises image drawing heads, moving means, active pixel specification means, and setting change means. Each of the image drawing heads faces the image drawing surface and comprises a pixel array. The pixel arrays of the image drawing heads respectively have usable pixels laid out two-dimensionally and generate image drawing spots forming the two-dimensional pattern according to the image data. The image drawing heads are laid out in such a manner that a direction of columns of the usable pixels forms a predetermined angle with a scanning direction of the image drawing heads. The moving means moves the image drawing heads relatively to the image drawing surface in the scanning direction. The active pixel specification means specifies, for each of the image drawing heads, active relay area pixels for realizing the N-overlay image drawing in an inter-head relay area in the image drawing surface, among usable relay area pixels corresponding to the image drawing spots in the inter-head relay area out of the usable pixels.

The setting change means changes a setting for causing only the active relay area pixels to operate among the usable relay area pixels for each of the image drawing heads.

The pixel columns in the present invention refers to lines of pixels aligned along the direction forming a smaller angle with the scanning direction, out of the two alignment directions of the two-dimensionally arranged pixels in each of the pixel arrays. "Pixel rows" refer to lines of pixels arranged along the direction forming a larger angle with the scanning direction. The pixels in each of the pixel arrays may not necessarily be placed in a rectangular grid shape. For example, the pixels may be laid out to form a parallelogram.

In the present invention, "N-overlay image drawing" refers to image drawing in such a manner that a line parallel to the scanning direction intersects with N lines of columns of the active pixels projected onto the image drawing surface in substantially all points in an image drawing range on the image drawing surface. The line intersects with the active-pixel columns in "substantially all points" in the predetermined range, since a pixel pitch along the direction perpendicular to the scanning direction does not strictly match with a pixel pitch of other parts due to an error in an installation angle or pixel positions in a tiny area smaller than resolution in a relay area between the columns of the active pixels. Therefore, in the tiny area, the number of the pixel columns intersecting with the line parallel to the scanning direction may change in the range of ±1. In the description below, N-overlay image drawing wherein N is two or larger is referred to as multiple-overlay image drawing. Furthermore, in an exposure apparatus or an exposure method as an embodiment of the image drawing apparatus or an image drawing method of the present invention, "N-overlay exposure" and "multiple-overlay exposure" are used as words corresponding to "N-overlay image drawing" and "multiple-overlay image drawing".

In the present invention, each of the inter-head relay areas refers to a part of an image drawing area in the image drawing surface covered by the pixel array in one of the image drawing heads, in which a coordinate along the direction perpendicular to the scanning direction matches with that in an image drawing area covered by the pixel array in another one of the image drawing heads.

The active pixel specification means in the present invention may receive manual specification of the active pixels. Alternatively, the active pixel specification means may comprise position detection means and selection means that will be described later for automatically selecting the active pixels optimally.

Changing the setting for causing only the active relay area pixels to operate refers to a manner of setting the pixels other than the active relay area pixels in the usable relay area pixels to be in an OFF state for stopping operation thereof. Alternatively, a part of the image data to be sent to the usable relay area pixels other than the active relay area pixels may represent data of OFF state (that is, data representing that the corresponding pixels do not participate in the image drawing). Furthermore, the setting may be changed to a state wherein an image drawing medium such as a light or an ink droplet from each of the usable relay area pixels other than the active relay area pixels is blocked although the usable relay area pixels other than the active relay area pixels are actually in operation.

In the image drawing apparatus of the present invention, the active pixel specification means may further specify active intra-area pixels out of the pixels other than the usable relay area pixels among the usable pixels for each of the image drawing heads, for realizing the N-overlay image drawing in areas other than the inter-head relay areas in the image drawing surface. In this case, the setting change means changes the setting for each of the image drawing heads in order to cause only the active intra-area pixels to operate out of the pixels other than the usable relay area pixels among the usable pixels.

In the image drawing apparatus of the present invention, it is preferable for an angle θ representing the predetermined angle of the image drawing heads to satisfy the following equation:

$$sp \sin \theta \geq N\delta$$

where s refers to the number of the pixels forming each of the columns of the usable pixels in each of the image drawing heads, p refers to a pitch of the usable pixels along the direction of the pixel columns, and δ refers to a pitch of the columns of the usable pixels projected onto a line perpendicular to the scanning direction.

In the image drawing apparatus of the present invention, it is preferable for N to be 2 or larger.

In the image drawing apparatus of the present invention, the pixel arrays of the respective image drawing heads may generate light spots as the image drawing spots. In this case, the active pixel specification means may comprise position detection means for detecting positions of the light spots forming the inter-head relay area in the image drawing surface among the light spots for each of the image drawing heads and selection means for selecting the active relay area pixels for each of the image drawing heads in such a manner that a sum of a part wherein drawing is redundant and a part wherein drawing is deficient compared to ideal N-overlay image drawing becomes minimal in each of the inter-head relay areas in the image drawing surface, based on a result of the detection by the position detection means.

Alternatively, in the case where the pixel arrays of the respective image drawing heads generate the light spots as the image drawing spots, the active pixel specification means may comprise position detection means for detecting positions of the light spots forming the inter-head relay area in the image drawing surface among the light spots for each of the image drawing heads and selection means for selecting the active relay area pixels for each of the image drawing heads in such a manner that the number of the image drawing spots in a part where drawing is redundant becomes the same as the number of the image drawing spots in a part where drawing is deficient compared to the ideal N-overlay image drawing in each of the inter-head relay areas in the image drawing surface, based on a result of the detection by the position detection means.

Alternatively, in the case where the pixel arrays of the respective image drawing heads generate the light spots as the image drawing spots, the active pixel specification means may comprise position detection means for detecting positions of the light spots forming the inter-head relay area in the image drawing surface among the light spots for each of the image drawing heads and selection means for selecting the active relay area pixels for each of the image drawing heads in such a manner that a part wherein drawing is redundant compared to the ideal N-overlay image drawing becomes minimal in each of the inter-head relay areas while a part wherein drawing is deficient compared to the ideal N-overlay image drawing is not observed, based on a result of the detection by the position detection means.

Alternatively, in the case where the pixel arrays of the respective image drawing heads generate the light spots as the image drawing spots, the active pixel specification means may comprise position detection means for detecting positions of the light spots forming the inter-head relay area in the image drawing surface among the light spots for each of the image drawing heads and selection means for selecting the active relay area pixels for each of the image drawing heads in such a manner that a part wherein drawing is deficient compared to the ideal N-overlay image drawing becomes minimal in each of the inter-head relay areas while a part wherein drawing is redundant compared to the ideal N-overlay image drawing is not observed, based on a result of the detection by the position detection means.

The image drawing apparatus of the present invention may further comprise reference image drawing means for carrying out reference image drawing by using only the pixels of every (N−1) columns among the usable relay area pixels for each of the image drawing heads, in order to specify the active relay area pixels by the active pixel specification means.

Alternatively, the image drawing apparatus of the present invention may comprise reference image drawing means for carrying out reference image drawing by using only the pixels comprising a group of adjoining pixel rows corresponding to 1/N of all the rows of the usable pixels among the usable relay area pixels for each of the image drawing heads, in order to specify the active relay area pixels by the active pixel specification means.

In the case where the number of the rows of the usable pixels is not divisible by N, the group of adjoining pixel rows corresponding to 1/N of the number of all the rows of the usable pixels may be a group of pixel rows corresponding to the number closest to 1/N or to the largest number smaller than 1/N, or to the smallest number larger than 1/N.

The image drawing apparatus of the present invention may further comprise data conversion means for converting the image data so as to cause a size of a predetermined portion in each of the inter-head relay areas in the two-dimensional pattern represented by the image data to match with a size of a corresponding portion formed by the active relay area pixels that have been specified.

In the image drawing apparatus of the present invention, the pixel arrays may be spatial light modulators that modulate light from a light source according to the image data for each of the pixels.

The light source may be incorporated into each of the image drawing heads (exposure heads). Alternatively, the light source may be installed outside the image drawing heads to be used by each of the image drawing heads or to be shared by a part of the image drawing heads.

An image drawing method of the present invention is a method of image drawing by using image drawing heads each facing an image drawing surface and comprising a pixel array. The pixel arrays respectively have usable pixels laid out two-dimensionally, and generate image drawing spots according to image data for forming a two-dimensional pattern represented by the image data. The image drawing heads are set in such a manner that a direction of columns of the usable pixels forms a predetermined angle with a direction of scanning by the image drawing heads. The image drawing method comprises the steps of:

specifying, for each of the image drawing heads, active relay area pixels for realizing N-overlay image drawing in an inter-head relay area in the image drawing surface, among usable relay area pixels corresponding to the image drawing spots in the inter-head relay area out of the usable pixels;

changing a setting of the image drawing heads so that only the active relay area pixels to operate out of the usable relay area pixels for each of the image drawing heads; and forming the two-dimensional pattern on the image drawing surface by causing the image drawing heads to operate with movement relative to the image drawing surface in the scanning direction.

Operating the image drawing heads with movement relative to the image drawing surface in the scanning direction refers to a manner of continuous image drawing by continuously moving the image drawing heads or to a manner of image drawing by moving the image drawing heads in a step-wise manner to a halt for drawing.

According to the image drawing apparatus and the image drawing method of the present invention, the pixels of a number and distribution that can minimize an influence of relative positions and angles between the image drawing heads can be specified as the active relay area pixels among the usable relay area pixels. Therefore, the N-overlay image drawing can be carried out while reducing unevenness in resolution and density occurring in the inter-head relay areas in the actual image drawing surface.

Furthermore, if the active pixel specification means specifies the active intra-area pixels for realizing the N-overlay image drawing in the areas other than the inter-head relay areas and if the setting change means changes the setting so that only the active intra-area pixels to operate out of the usable pixels other than the usable relay area pixels, the active intra-area pixels can be specified so as to have the quantity and distribution that can minimize an effect of an error in the installation angle of the image drawing heads and pattern distortion in the areas other than the inter-head relay areas. Therefore, uniform N-overlay image drawing can be carried out, reducing unevenness in resolution and density over the entire image drawing surface.

Moreover, if N is two or larger to realize multiple-overlay image drawing, a filling effect of multiple-overlay image drawing can smooth inevitable unevenness smaller than resolution and effects caused by residual errors in relative positions between the image drawing heads and in the installation angle thereof, as well as an effect caused by pattern distortion. Therefore, residual unevenness in resolution and density in the two-dimensional pattern can be reduced further.

If reference image drawing can be carried out by using only the pixels comprising every (N−1) pixel columns, or the adjoining pixel rows corresponding to 1/N of all the rows of usable pixels, reference image drawing can generate a simple pattern approximately with no overlap. Therefore, specification of the active relay area pixels can be easier through confirmation or the like of the pattern by an operator, which leads to easier and optimal specification of the active relay area pixels.

If the image data are converted for agreement between the sizes of the predetermined parts, the size of the two-dimensional pattern represented by the image data can be equal to the size of the predetermined part that can be formed by the active relay area pixels having been specified. Therefore, the two-dimensional pattern can be formed on the image drawing surface in high definition as desired.

BRIEF DESCRIPTION OF THE DRAWINGS

FIG. 3A is a top view representing exposed areas formed on an exposure surface of a photosensitive material while

FIGS. 5A and 5B are a top view and a side view showing in detail the configuration of each of the exposure heads in the exposure apparatus;

FIG. 6 is a partial enlargement showing the configuration of a DMD in the exposure apparatus;

FIG. 8 is a perspective view showing the configuration of a fiber-array light source;

FIG. 9 is a frontal view showing layout of light emission points in a laser emission area in the fiber-array light source;

DESCRIPTION OF THE PREFERRED EMBODIMENTS

Hereinafter, an exposure apparatus as an embodiment of an image drawing apparatus of the present invention will be described in detail with reference to the accompanying drawings.

Figure 1:
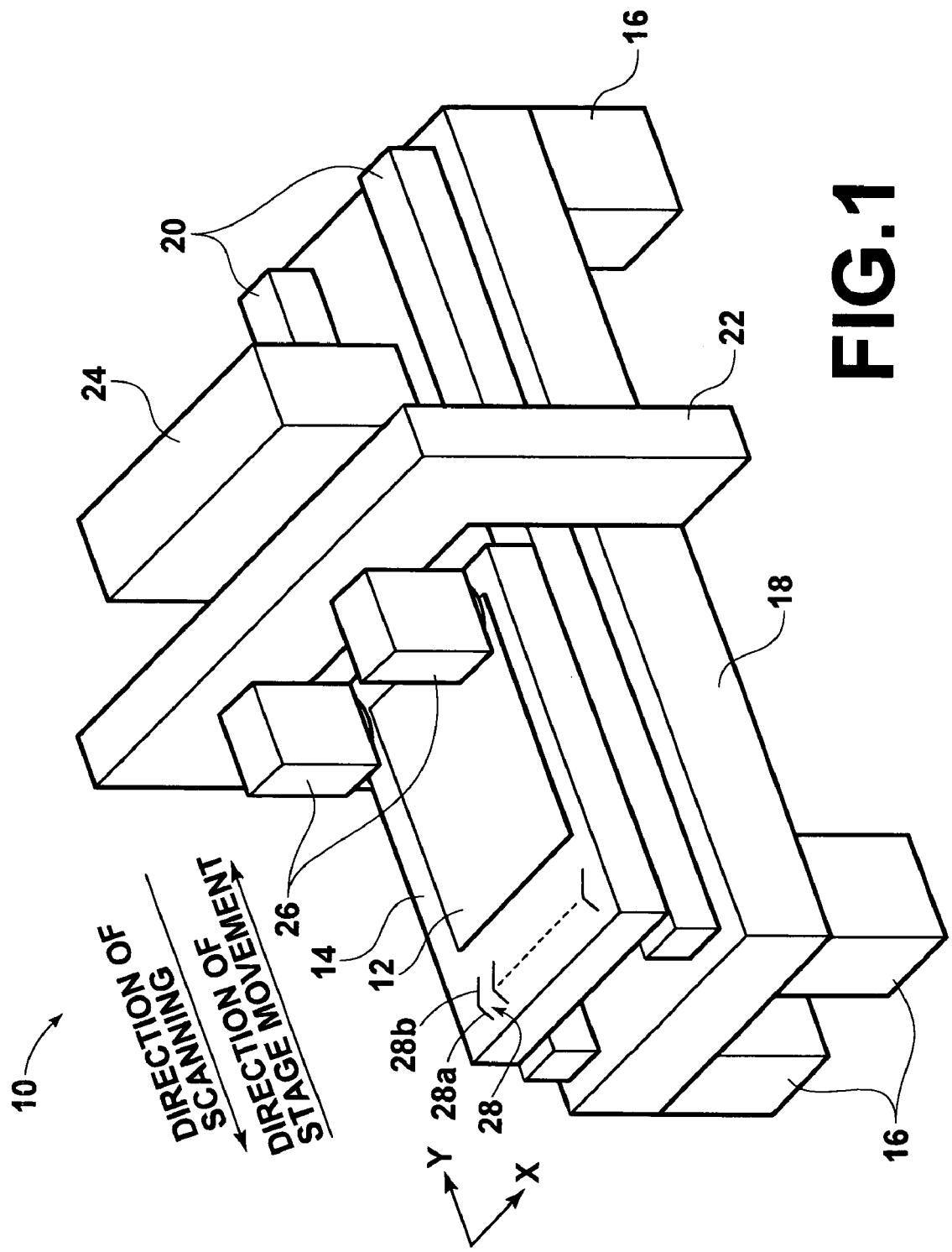
FIG. 1 is a perspective view representing the appearance of an exposure apparatus as an embodiment of an image drawing apparatus of the present invention.

As shown in FIG. 1, an exposure apparatus 10 of this embodiment comprises a planar stage 14 for holding a sheet 12 of photosensitive material (hereinafter referred to as the photosensitive sheet 12) by suction. On the upper surface of a thick plate-like mount 18 supported by four legs 16 are placed two guide rails 20 elongated along the direction of movement of the stage 14. The stage 14 is placed in such a manner that the direction of longer sides thereof is parallel to the direction of movement thereof. The stage 14 is supported by the guide rails 20 so that the stage 14 can move back and forth along the rails. The exposure apparatus 10 also comprises a stage driving unit (not shown) for driving the stage 14 along the guide rails 20.

A U-shaped gate 22 is situated at the center of the mount 18 so as to straddle the path of the stage 14. Both ends of the U-shaped gate 22 are fixed to side faces of the mount 18. A scanner 24 is located beside the U-shaped gate 22 while a plurality (such as 2) of sensors 26 are placed opposite to the scanner 24 across the gate 22. The sensors 26 detect front and rear ends of the photosensitive sheet 12. The scanner 24 and the sensors 26 are attached to the gate 22 at fixed positions around the start of forward movement of the stage 14. The scanner 24 and the sensors 26 are connected to a controller (not shown) thereof. As shown in FIG. 1, an X axis and a Y axis that are perpendicular to each other are defined to aid the description, in a plane parallel to the surface of the stage 14.

On one end of the stage 14 at which scanning ends are formed nine L-shaped slits 28 placed at regular intervals. The corners of the slits are aligned along the direction of the X axis. Each of the slits 28 has a slit 28$a$ located closer to the end of the stage 14 and a slit 28$b$ located farther from the end. The slits 28$a$ and 28$b$ are perpendicular to each other in the respective slits 28, and the slit 28$a$ forms an angle of −45 degrees with the X axis while the slit 28$b$ forms an angle of 45 degrees. Single cell photo detectors (not shown) are located respectively under the slits 28 in the stage 14. Each of the photo detectors is connected to a processor (not shown) for carrying out active pixel selection processing that will be described later.

Figure 2:
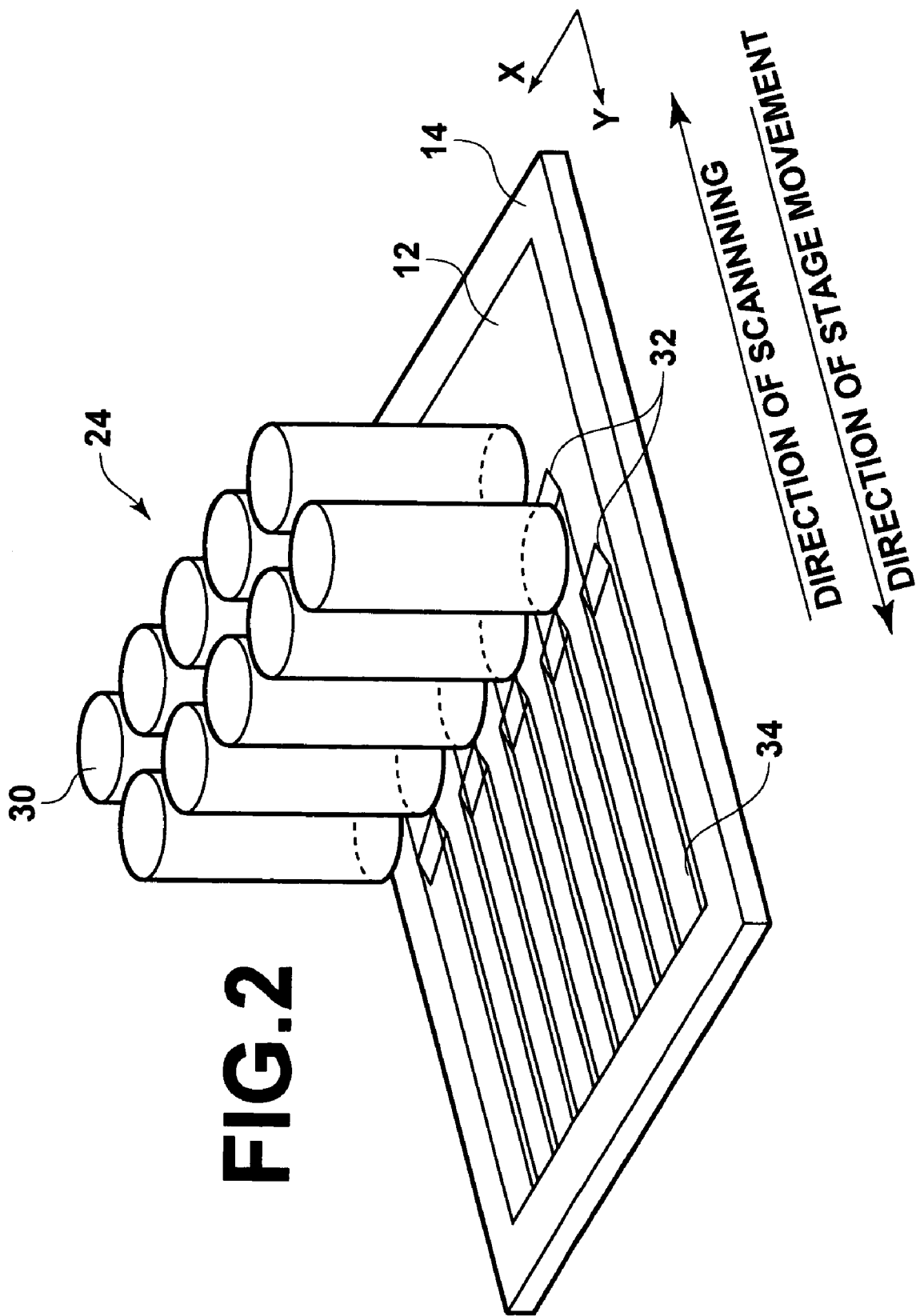
FIG. 2 is a perspective view of the configuration of a scanner in the exposure apparatus shown in FIG. 1.
Figure 3A:
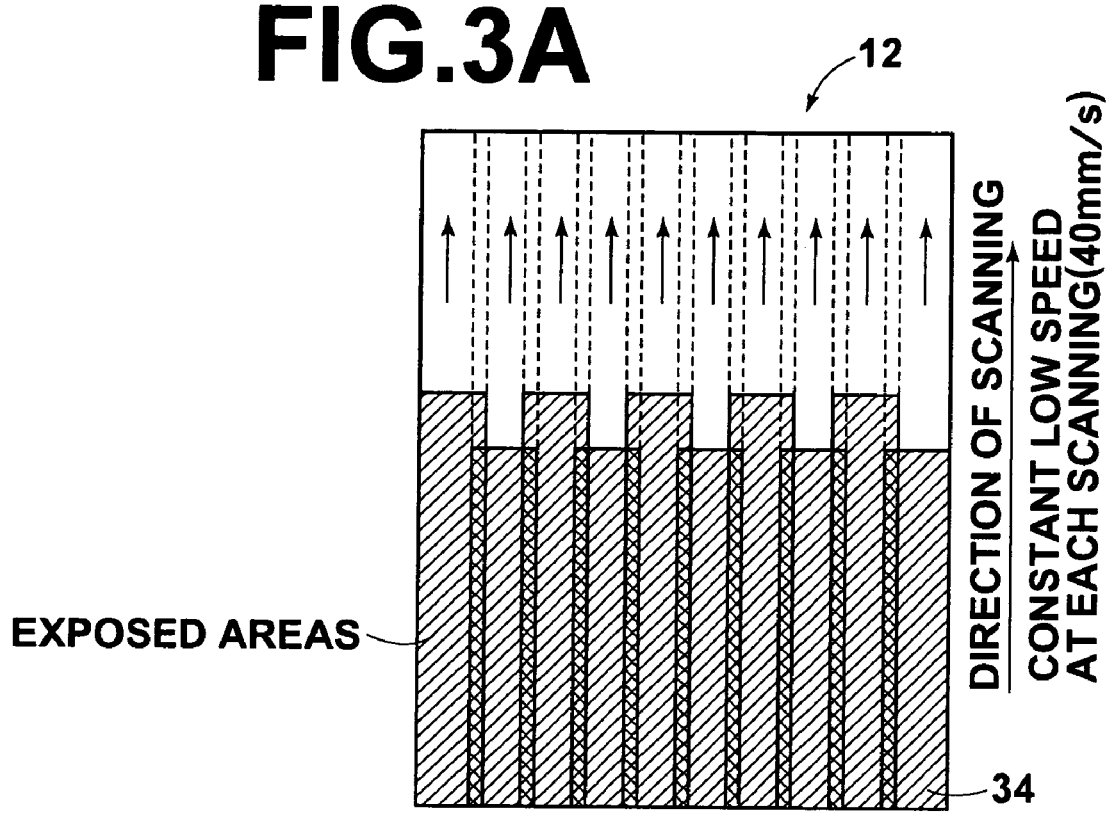
Figure 3B:
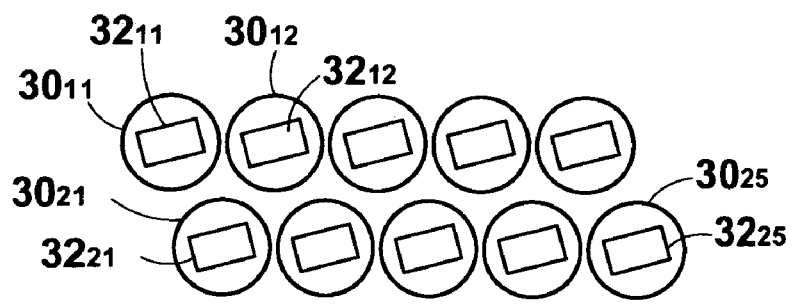
FIG. 3B is a top view showing arrangement of exposure areas of exposure heads.

The scanner 24 comprises 10 exposure heads 30 laid out in a shape close to a matrix of 2 rows and 5 columns, as shown in FIG. 2 and FIG. 3B. Hereinafter, one of the exposure heads 30 located in an $m^{th}$ row in an $n^{th}$ column is expressed as an exposure head 30$_{mn}$.

Each of the exposure heads 30 is installed in the scanner 24 in such a manner that the direction of pixel rows in a digital micro-mirror device (DMD) 36 therein forms a predetermined angle θ with the direction of scanning. Therefore, an exposure area 32 of each of the exposure heads 30 is shaped into a rectangle that is diagonal to the direction of scanning. Following the movement of the stage 14, a strip of exposed area 34 corresponding to each of the exposure heads 30 is formed on an exposure surface of the photosensitive sheet 12. Hereinafter, an exposure area 32$_{mn}$ refers to an exposure area of the exposure head 30$_{mn}$.

As shown in FIGS. 3A and 3B, each of the exposure heads 30 is placed so that the exposed area 34 thereof partially overlaps with the neighboring exposed areas 34. Therefore, an area between the exposure areas 32$_{11}$ and 32$_{12}$ that cannot be exposed by the exposure heads in the first row can be exposed by the neighboring exposure area 32$_{21}$ in the second row.

The positions of the nine slits 28 are substantially matched with the center of the respective overlaps of the neighboring exposed areas 34. A size of each of the slits 28 is sufficient enough for covering a width of the overlaps between the exposed areas 34.

Figure 4:
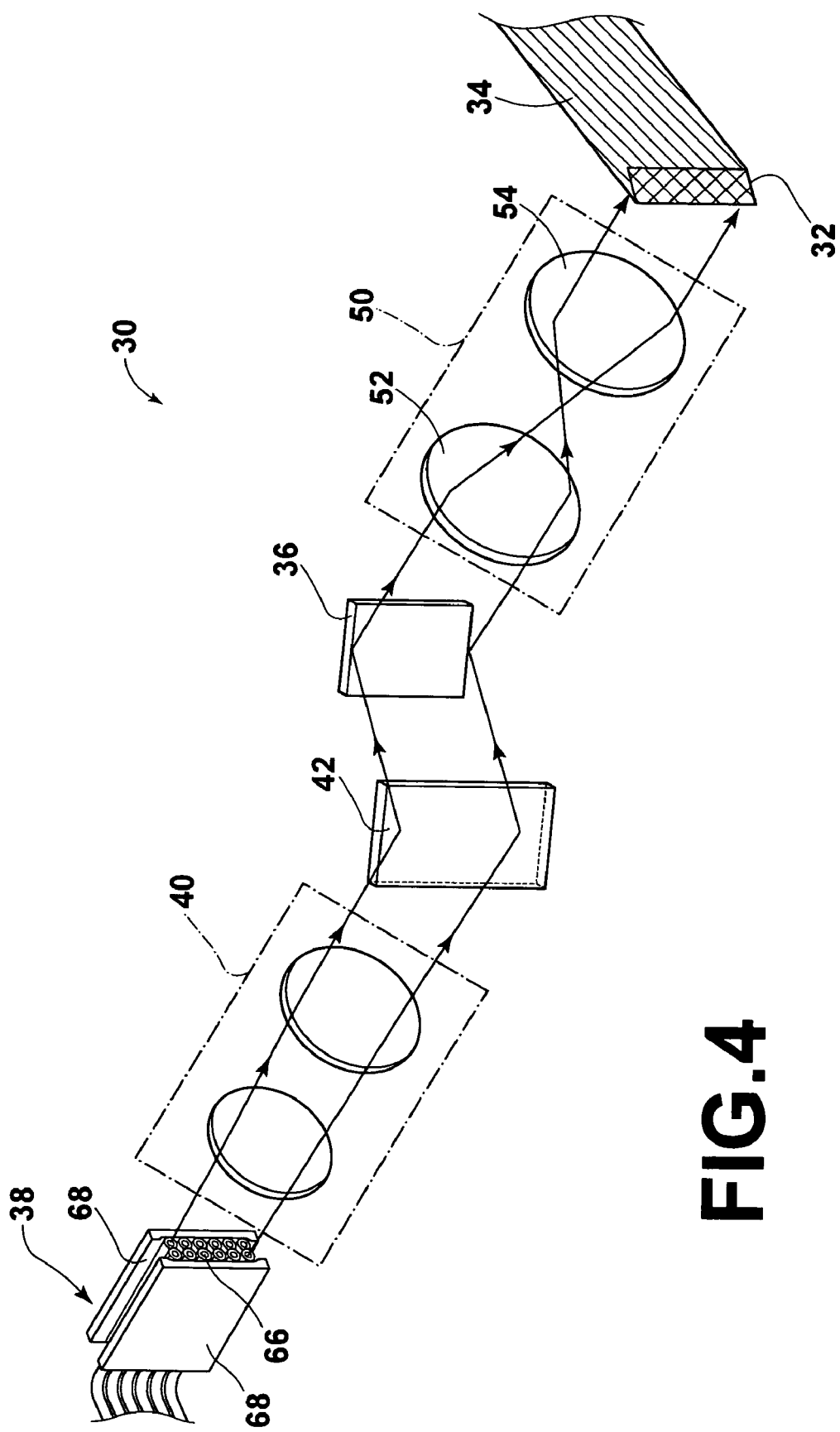
FIG. 4 is a perspective view of the configuration of each of the exposure heads in the exposure apparatus shown in FIG. 1.

As shown in FIGS. 4 and 5, each of the exposure heads 30 comprises the DMD' 36 manufactured by Texas Instruments Incorporated in U.S., as spatial light modulators for respective pixels that modulate an incident light according to image data. Each of the DMD's 36 is connected to a controller comprising a data processing unit and a mirror driving control unit. The data processing unit in the controller generates a control signal for controlling driving of each of micro-mirrors in a usable area of the corresponding DMD 36 in the corresponding exposure head 30. The mirror driving control unit controls an angle of reflection surface for each of the micro-mirrors in the corresponding DMD 36 of the corresponding exposure head 30, according to the control signal generated by the data processing unit.

As shown in FIG. 4, a fiber-array light source 38, a lens system 40, and a mirror 42 are placed in this order on one side of each of the DMD's 36 from which the light enters. The fiber-array light source 38 comprises a laser emission area in which light emission end facets (light emission points) of optical fibers are aligned along the direction of a longer side of the corresponding exposure area 32. The lens system 40 causes laser beams emitted from the fiber-array light source 38 to focus on the corresponding DMD 36. The mirror 42 reflects the laser beams having passed through the lens system 40 toward the corresponding DMD 36. In FIG. 4, the configuration of the lens system 40 is outlined.

The lens system 40, shown in FIG. 5 in detail, comprises a combination lens pair 44, a combination lens pair 46, and a condensing lens 48. The combination lens pair 44 causes the laser beams emitted from the fiber-array light source 38 to be come parallel lights. The combination lens pair 46 causes the parallel lights to have uniform distribution in the amount of light. The condensing lens 48 causes the lights to focus on the corresponding DMD 36.

A lens system 50 is situated on the other side of the corresponding DMD 36 from which the reflected lights come. The lens system 50 is used for causing the reflected lights from the corresponding DMD 36 to focus on the exposure surface of the photosensitive sheet 12. The lens system 50 comprises two lenses 52 and 54 laid out in such a manner that conjugate focal planes are formed on the corresponding DMD 36 and on the exposure surface of the photosensitive sheet 12.

After the laser beams emitted from the fiber-array light source 38 are magnified by 5 times, a portion thereof from each of the micro-mirrors in the corresponding DMD 36 is narrowed to approximately 5 μm by the lens system 50.

As shown in FIG. 6, each of the DMD's 36 is a mirror device having micro-mirrors 58 comprising the pixels laid out in a grid-like pattern on SRAM cells (memory cells). In this embodiment, each of the DMD's 36 has the micro-mirrors 58 of 768 rows and 1024 columns. However, only the micro-mirrors of 256 rows and 1024 columns can be driven by the controller connected to the corresponding DMD 36 and are therefore usable. A data processing speed of the DMD's 36 is limited, and a modulation speed per line is determined according to the number of the micro-mirrors to be used. Therefore, by using only a part of the micro-mirrors, the modulation speed per line becomes faster. Each of the micro-mirrors 58 is supported by a post and the surface thereof is coated with a material having high reflectivity, such as aluminum, by vapor deposition thereof. In this embodiment, the reflectivity of each of the micro-mirrors 58 is more than 90%, and a pitch between the micro-mirrors is 13.7 μm in the horizontal direction and in the vertical direction. The SRAM cells 56 comprise CMOS'es each having a silicon gate produced in an ordinary semi-conductor memory production line with the post including hinges and yokes. The entire SRAM cells 56 are configured in a mono-lithic (unified) manner.

Figure 7A:
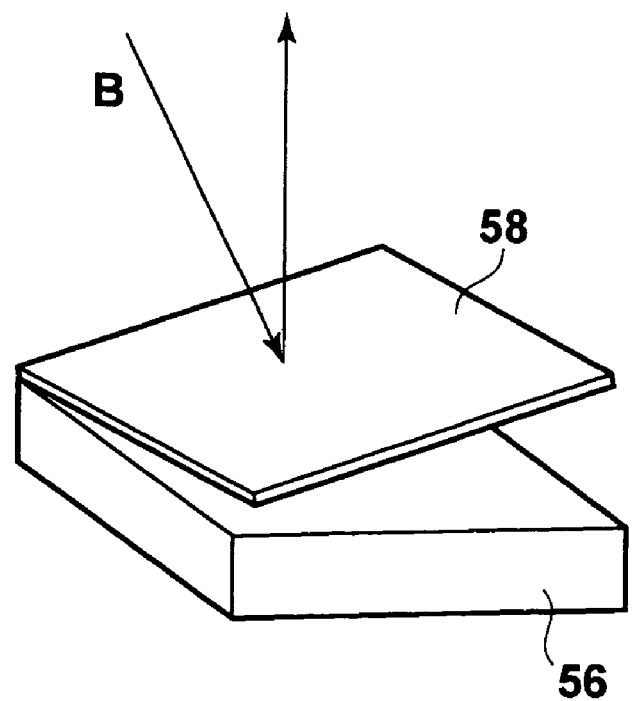
FIGS. 7A and 7B show operation of the DMD.
Figure 7B:
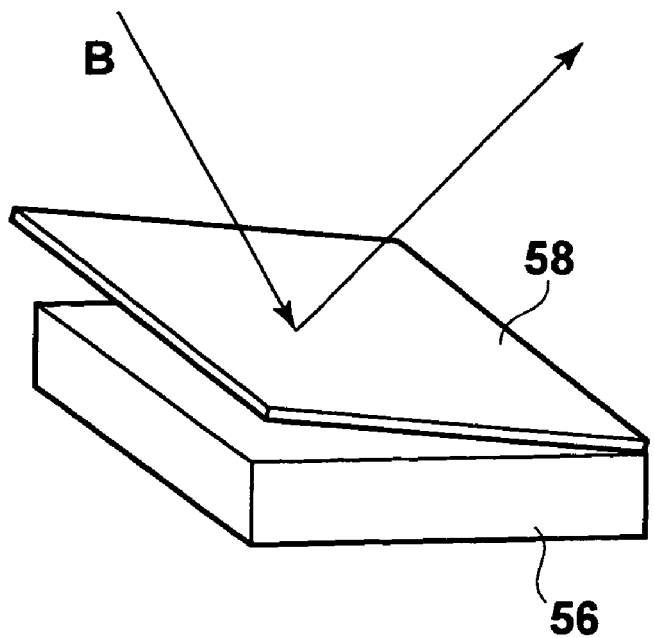

When an image signal as digital data representing density of respective points comprising a desired two-dimensional pattern is written in the SRAM cells 56 in each of the DMD's 36, each of the micro-mirrors 58 supported by the post tilts relatively to the substrate on which the corresponding DMD 36 is formed, in an angle of −α or +α degrees (such as −10 or +10 degrees) around a diagonal line thereof. FIG. 7A shows an ON state wherein one of the micro-mirrors 58 is tilted by α degrees while FIG. 7B shows an OFF state wherein the micro-mirror 58 is tilted by −α degrees. Therefore, by controlling the tilt of the respective micro-mirrors 58 at the pixels in each of the DMD's 36 according to the image signal as shown in FIG. 6, a laser beam B that has reached the corresponding DMD 36 is reflected toward the tilt of the micro-mirror 58.

FIG. 6 shows a partial enlargement of each of the DMD's 36, and represents a state wherein each of the micro-mirrors 58 is controlled to be in the tilt of −α or +α degrees. The ON or OFF state of the micro-mirrors 58 is controlled by the controller connected to the corresponding DMD 36. A light absorber (not shown) is situated in the direction of the lease beam B reflected by each of the OFF-state micro-mirrors 58.

The fiber-array light source 38 comprises a plurality of laser modules 60 (such as 14 modules), as shown in FIG. 8. Each of the laser modules 60 is coupled with one end of a multiple-mode optical fiber 62. A multiple-mode optical fiber 64 having a cladding diameter smaller than that of the optical fibers 62 is also connected to the other end of each of the multiple-mode optical fibers 62. As shown in FIG. 9 in detail, a laser emission area 66 is configured by the other end of each of the multiple-mode optical fibers 64, and two lines each comprising 7 of the ends are laid out in the direction perpendicular to the direction of scanning.

The laser emission area 66 comprising the other end of each of the multiple-mode optical fibers 64 is fixed by being sandwiched with two support plates 68 each having a flat surface, as shown in FIG. 9. It is preferable for light emission end facets of the multiple-mode optical fibers 64 to be protected by a transparent plate such as glass. Since the light emission end facets of the multiple-mode optical fibers 64 tend to be degraded due to dust deposition thereon caused by high density of light, deposition of dust on the end facets and degradation thereof can be delayed by using the plate for protection.

Hereinafter, the active pixel specification processing in the exposure apparatus 10 in this embodiment will be described with reference to FIGS. 10 to 13.

In this embodiment, 2-overlay exposure is carried out by the exposure apparatus 10. As the predetermined angle of each of the exposure heads 30, that is, each of the DMD's 36, is adopted an angle $\theta_{ideal}$ realizing 2-overlay exposure by using the usable micro-mirrors 58 of 256 rows and 1024 columns in an ideal state wherein no error in installation angle or the like is found in the exposure heads 30. The angle $\theta_{ideal}$ is found by Equation (1) below:

$$sp \sin \theta_{ideal} = N\delta \quad (1)$$

where N refers to the number N of N-overlay exposure, s refers to the number of the micro-mirrors 58 comprising each of pixel columns of the usable micro-mirrors 58, p is a pixel pitch in the direction of the columns of the micro-mirrors 58, and δ refers to a pixel pitch in each of the pixel columns of the usable micro-mirrors 58 projected onto a line perpendicular to the direction of scanning. Each of the DMD's 36 in this embodiment comprises the micro-mirrors 58 laid out in the form of rectangular grid whose pitches in the horizontal and vertical directions are the same, as has been described above. Therefore, Equation (2) below is satisfied:

$$p \cos \theta_{ideal} = \delta \quad (2)$$

Consequently, Equation (3) below can be obtained from Equations (1) and (2):

$$s \tan \theta_{ideal} = N \quad (3)$$

In this embodiment, s=256 and N=2. Therefore, $\theta_{ideal}$=0.45 degree can be found from Equation (3). The exposure apparatus 10 has been initially adjusted to cause the installation angle of the exposure heads 30, that is, the DMD's 36, to become $\theta_{ideal}$.

Figure 10:
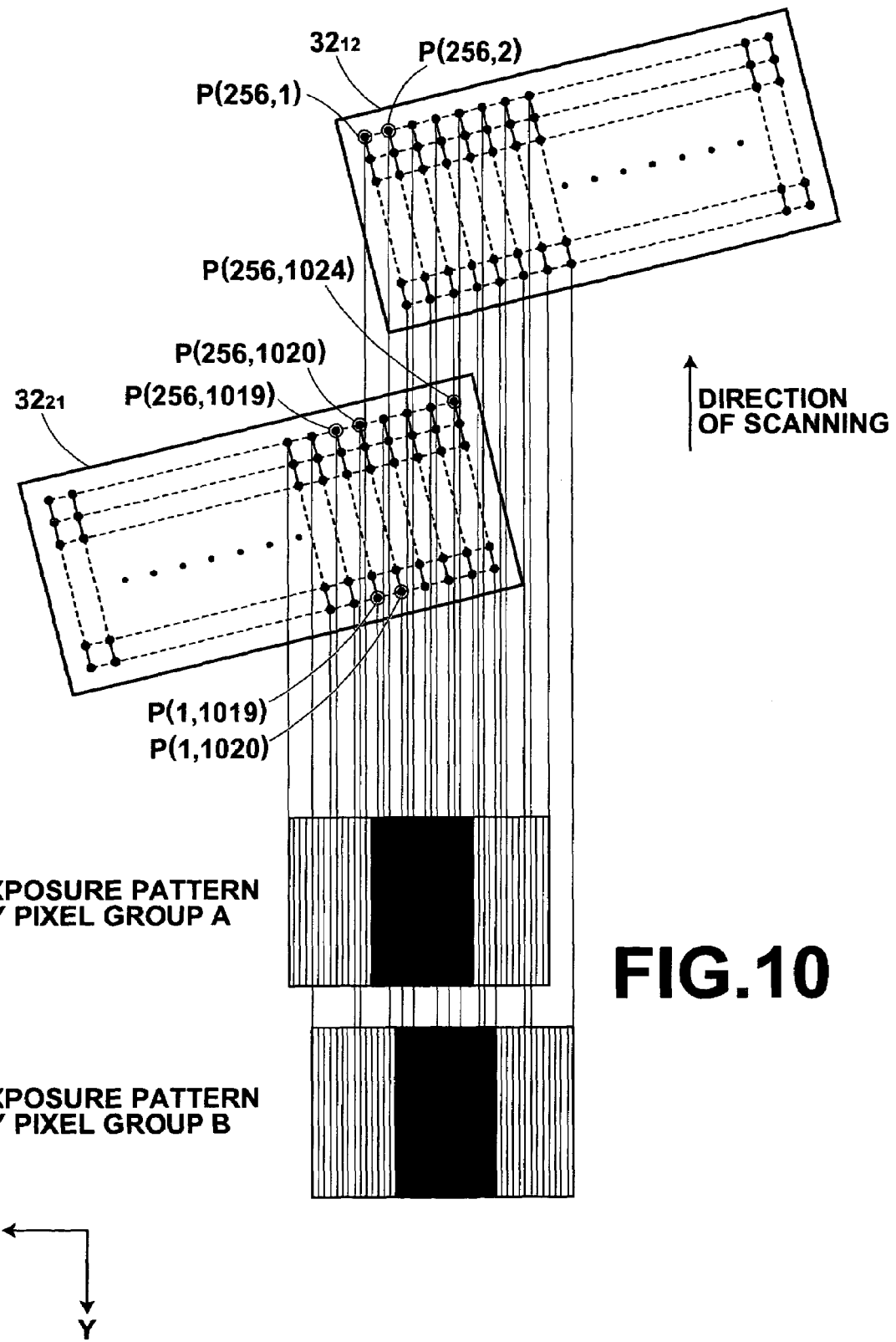
FIG. 10 shows an example of unevenness in patterns in the exposure surface caused by deviation of relative positions of exposure heads that are adjacent to each other.

FIG. 10 shows an example of unevenness in a pattern on the exposure surface generated by the exposure apparatus 10 having been initially adjusted in the above manner, and the unevenness is generated by an effect of deviation from an ideal state in relative positions between two of the exposure heads 30 (such as the exposure heads $30_{12}$ and $30_{21}$) in the X axis direction. The deviation in the X axis direction can be caused by difficulty in fine adjustment of the relative positions between the exposure heads.

Figure 11:
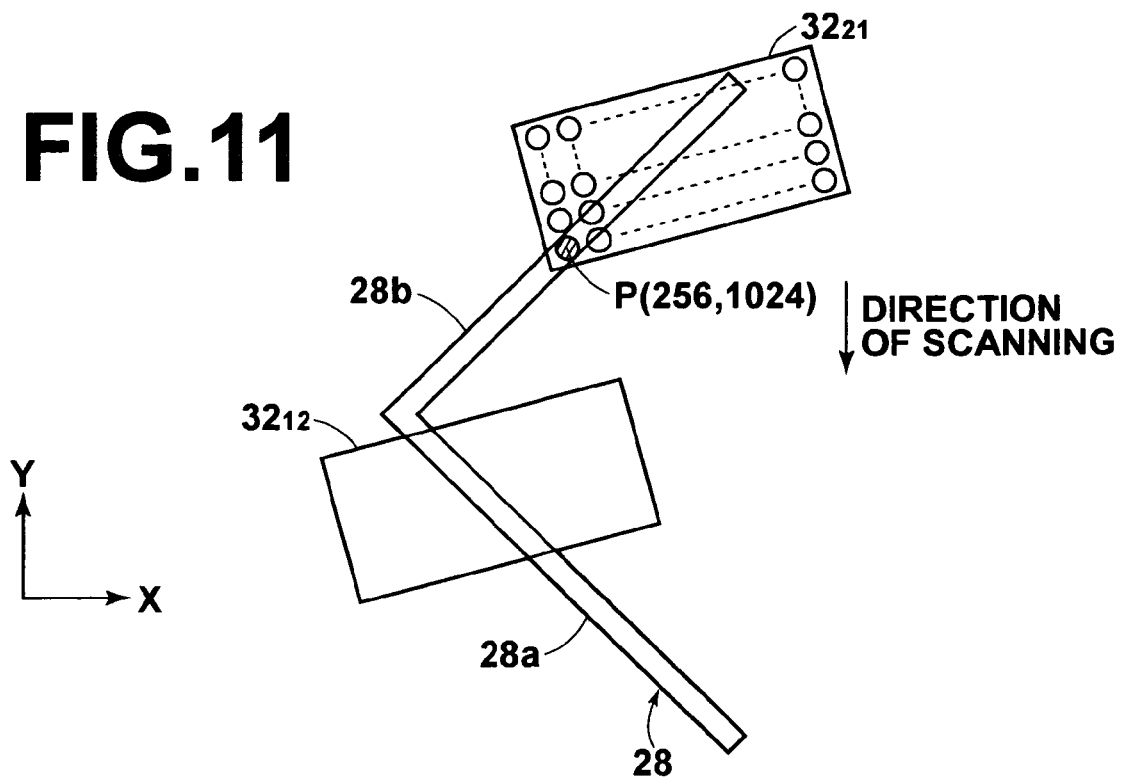
FIG. 11 is a top view representing a relationship between positions of the exposure areas of two adjacent exposure heads and corresponding slits.

In the description below and in FIGS. 11 to 13, an $m^{th}$ row of light spots of each of the exposure areas 32 in the exposure surface is referred to as r(m) while an $n^{th}$ column of light spots in the exposure surface is referred to as c(n). A light spot in the $m^{th}$ row in the $n^{th}$ column is referred to as P(m,n). An upper part of FIG. 10 shows patterns of the light spots from the usable micro-mirrors 58 in the DMD's 36 of the exposure heads $30_{12}$ and $30_{21}$ projected onto the exposure surface of the photosensitive sheet 12 when the stage 14 is stationary. A lower part of FIG. 10 shows exposure patterns regarding an inter-head relay area between the exposure areas $32_{12}$ and $32_{21}$ and the vicinity thereof. The exposure patterns are formed on the exposure surface when the stage 14 is moved for continuous exposure in a state where the patterns of the light spots shown in the upper part of FIG. 10 are formed. For the sake of easier understanding, the exposure patterns in FIG. 10 are shown separately for a pixel group A comprising the pixels of every other column of the usable micro-mirrors 58 and for a pixel group B comprising the pixels of the remaining columns. However, the actual exposure pattern appearing on the exposure surface is a pattern generated by superposition of the two patterns.

In the example shown in FIG. 10, areas of redundant exposure compared to ideal 2-overlay exposure appear in the inter-head relay area between the exposure areas $32_{12}$ and $32_{21}$ for both the exposure patterns by the pixel groups A and B, due to deviation from the ideal state of relative positions between the exposure heads $30_{12}$ and $30_{21}$ in the direction of X axis.

In order to reduce unevenness in the inter-head relay area on the exposure surface, positions are detected in the exposure surface regarding some of the light spots from the exposure heads $30_{12}$ and $30_{21}$ comprising the inter-head relay area, by the combination of the slit and the photo detector in this embodiment. Based on a result of the position detection, the processor connected to the photo detector carries out the processing for selecting active relay area pixels (the micro-mirrors 58 to be actually used for exposure processing) from the micro-mirrors 50 corresponding to the light spots comprising the inter-head relay area between the exposure heads $30_{12}$ and $30_{21}$.

How the position detection regarding the light spots is carried out by the combination of the slit 28 and the photo detector will be described below with reference to FIGS. 11 and 12. FIG. 11 is a top view representing a relationship between the positions of the exposure areas $32_{12}$ and 3221 shown in FIG. 10 and the corresponding slit 28. As has been described above, the size of the slit 28 is sufficiently large for covering the width of the overlap between the exposed areas 34 generated by the exposure heads $30_{12}$ and $30_{21}$. In other words, the slit 28 is large enough to cover the inter-head relay area.

Figure 12:
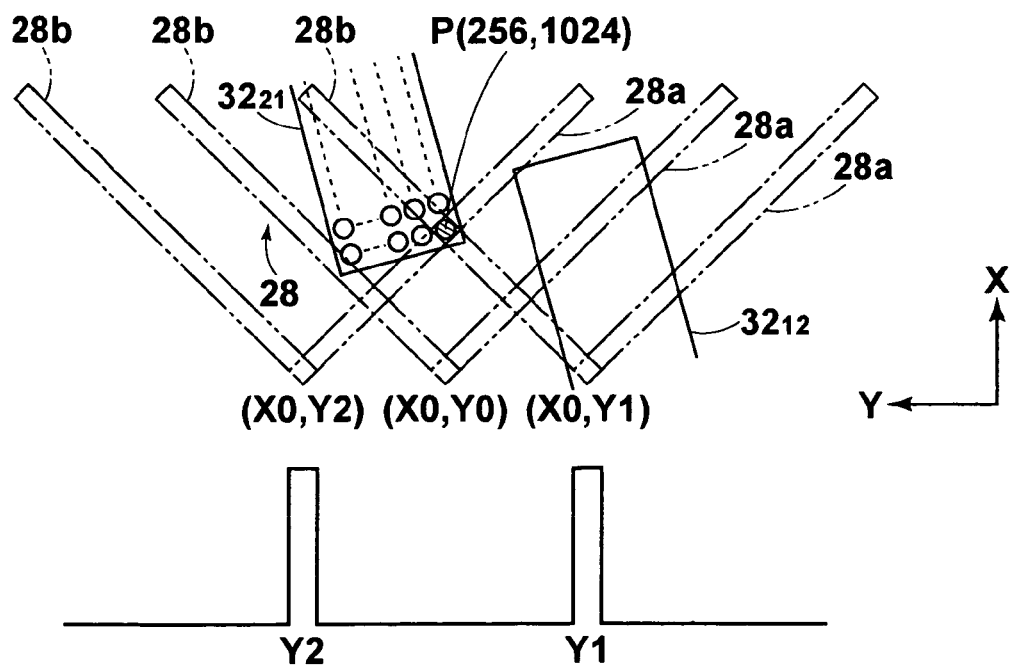
FIG. 12 is a top view for explaining a method of measuring positions of light spots in the exposure surface by using the slits.

FIG. 12 is a top view showing how the position of the light spot P(256,1024) in the exposure area $32_{21}$ is detected. The stage 14 is slowly moved for causing the slit 28 to move along the Y axis while the light spot P(256, 1024) is turned on. The slit 28 is positioned so as to cause the light spot P(256, 1024) to come any position between the slits 28a and 28b. The coordinates of the intersection between the slits 28a and 28b are expressed as (X0, Y0). The values of (X0, Y0) are determined and recorded based on a move distance by the stage 14 to the position, which is represented by a driving signal given to the stage 14, and based on the position of the slit 28 in the X-axis direction that is already known.

Thereafter, the stage 14 is moved to cause the slit 28 to move along the Y axis to the right of FIG. 12. As shown by chain double-dashed lines in FIG. 12, the stage 14 is stopped when the light of the light spot P(256, 1024) is detected by the photo detector after passing through the slit 28b on the left. The coordinates of the intersection of the slits 28a and 28b are recorded as (X0, Y1).

Thereafter, the stage 14 is moved in the opposite direction to cause the slit 28 to move along the Y axis to the left of FIG. 12. As shown by chain double-dashed lines in FIG. 12, the stage 14 is stopped when the light of the light spot P(256, 1024) is detected by the photo detector after passing through the slit 28a on the right. The coordinates of the intersection of the slits 28a and 28b are recorded as (X0, Y2).

The coordinates (X, Y) of the light spot P(256, 1024) are determined as:

$$X=X0+(Y1-Y2)/2\ Y=(Y1+Y2)/2$$

based on the measurement described above.

For selection of the active relay area pixels, the combination of the slit 28 and the photo detector detects a position of the light spot P(256, 1) in the exposure area $32_{12}$ in the example shown in FIG. 10. Positions of the light spots of the row r(256) in the exposure area $32_{21}$ are then detected serially in order of P(256, 1024), P(256, 1023), P(256, 1022) and so on. This position detection is stopped when the light spot P(256, n) having the X coordinate larger than that of the light spot P(256, 1) is found in the exposure area $32_{12}$. The micro-mirrors corresponding to the light spots comprising the columns c(n+1) to c(1024) in the exposure area $32_{21}$ are determined as the micro-mirrors that area not used for actual exposure. In the example in FIG. 10, for example, if the detection is stopped in the case where the light spot P(256, 1020) in the exposure area $32_{21}$ is detected when the light spot P(256, 1020) has the X coordinate larger than the light spot P(256, 1) in the exposure area $32_{12}$, a hatched area 70 shown in FIG. 13 corresponding to the micro-mirrors for the light spots comprising the columns c(1021) to c(1024) in the exposure area $32_{21}$ are specified as the micro-mirrors that are not used for actual exposure.

A position of the light spot P(256, N) in the exposure area $32_{12}$ is detected according to the number N of the N-overlay exposure. In this embodiment, N=2. Therefore, the position of the light spot P(256, 2) is detected. Positions are detected serially in order of P(1, 1020), P(2, 1020), P(3, 1020) and so on regarding the light spots comprising the column c(1020) in the exposure area $32_{21}$ in the far right among the columns excluding the columns corresponding to the micro-mirrors that are not used in actual exposure, and the position detection is stopped when the light spot P(m, 1020) having the X coordinate larger than the light spot P(256, 2) in the exposure area $32_{12}$ is detected. Thereafter, the processor connected to the photo detector compares the X coordinate of the light spot P(256, 2) in the exposure area $32_{12}$ and the X coordinate of the light spots P(m, 1020) and P(m−1, 1020) in the exposure area $32_{21}$. In the case where the X coordinate of the light spot P(m, 1020) in the exposure area $32_{21}$ is closer to the X coordinate of the light spot P(256, 2) in the exposure area $32_{12}$, the micro-mirrors corresponding to the light spots P(1, 1020) to P(m−1, 1020) in the exposure area $32_{21}$ are determined as the micro-mirrors that are not used for actual exposure. In the case where the X coordinate of the light spot P(m−1, 1020) in the exposure area $32_{21}$ is closer to the X coordinate of the light spot P(256, 2) in the exposure area $32_{12}$, the micro-mirrors corresponding to the light spots P(1, 1020) to P(m−2, 1020) in the exposure area $32_{21}$ are determined as the micro-mirrors that are not used for actual exposure. The processing of position detection and selection of the micro-mirrors is carried out in the same manner regarding a position of the light spot P(256, N−1), that is, P(256, 1) in the exposure area $32_{12}$ and positions of the light spots comprising the neighboring column c(1019) in the exposure area $32_{21}$. Consequently, the micro-mirrors corresponding to the light spots comprising a cross-hatched area 72 in FIG. 13 are additionally determined as the micro-mirrors that are not used for actual exposure, for example. A signal is sent to the micro-mirrors having been specified as the micro-mirrors that area not used for actual exposure, for setting the angle thereof to be in the OFF state. The specified micro-mirrors are actually not used for actual exposure.

By selecting the micro-mirrors that are not used for actual exposure in the above manner, a sum of the areas of overexposure and underexposure compared to ideal 2-overlay exposure (hereinafter referred to as an overexposed area and an underexposed area) can be minimal can be minimized in the inter-head relay area between the exposure areas $32_{12}$ and $32_{21}$. As a result, uniform 2-overlay exposure that is extremely close to the ideal state can be realized, as shown in the lower part of FIG. 13.

Figure 13:
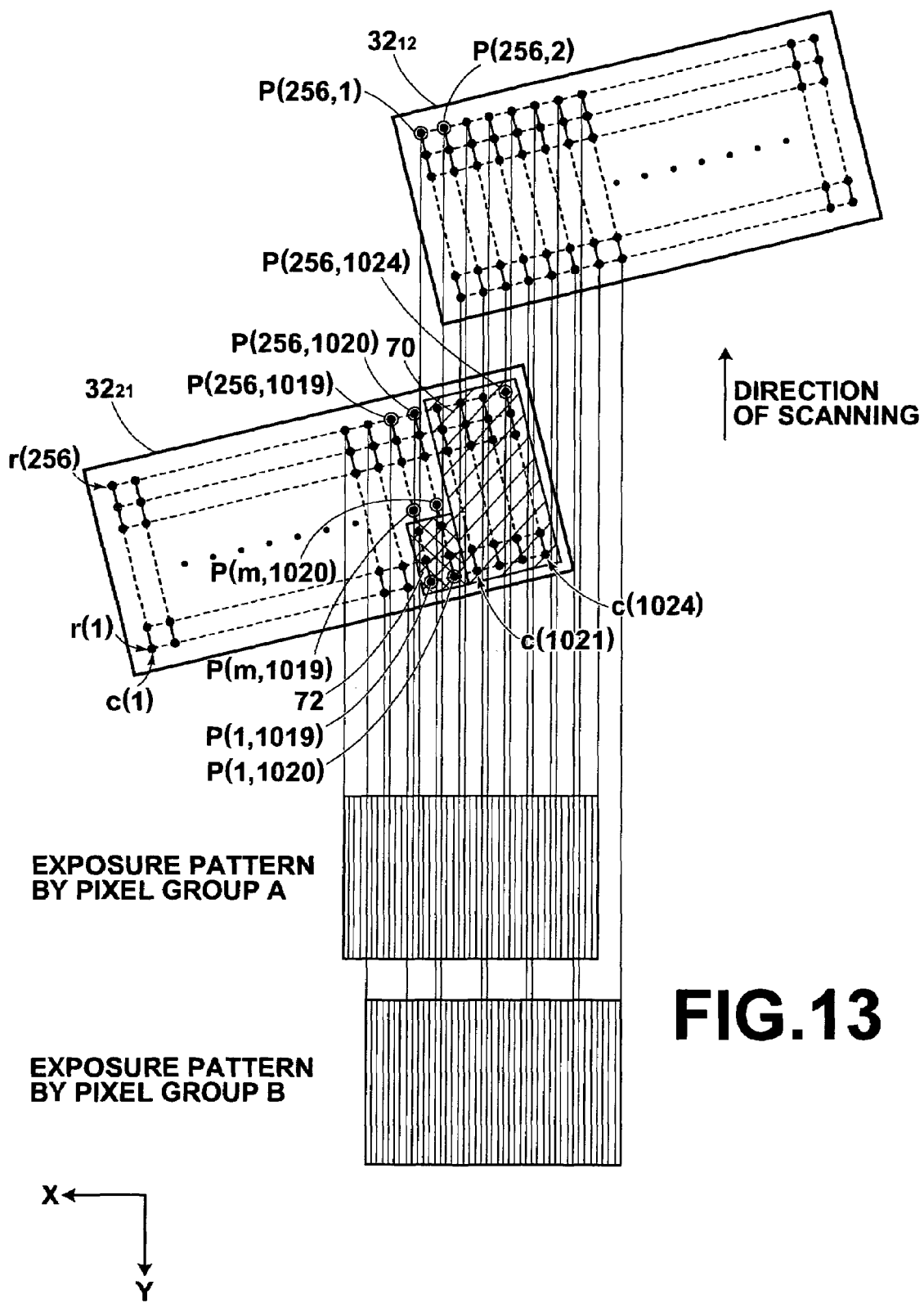
FIG. 13 shows a state of alleviated unevenness in the pattern in the exposure surface by operating only pixels selected in the example shown in FIG. 10.

In the example described above, when the light spots comprising the cross-hatched area 72 in FIG. 13 are found, the micro-mirrors corresponding to the light spots P(1, 1020) to P(m−2, 1020) in the exposure area $32_{21}$ may be determined immediately as the micro-mirrors that are not used, without comparing the X coordinate of the light spots P(m, 1020) and P(m−1, 1020) in the exposure area $32_{21}$ to the X coordinate of the light spot P(256, 2) in the exposure area $32_{12}$. In this case, the micro-mirrors causing the area of overexposure to become minimal and causing the area of underexposure to be absent in the inter-head relay area can be selected as the micro-mirrors to be actually used. Alternatively, the micro-mirrors corresponding to the light spots from P(1, 1020) to P(m−1, 1020) in the exposure area $32_{21}$ maybe used as the micro-mirrors that are not used for actual exposure. In this case, the micro-mirrors causing the area of underexposure to become minimal and causing the area of overexposure to be absent in the inter-head relay area can be selected as the micro-mirrors to be used practically. Alternatively, the micro-mirrors to be used may be selected so as to cause the number of the light spots in the overexposure area to be the same as the number of the light spots in the underexposure area.

An example of modified pixel specification processing in the exposure apparatus 10 described above will be described next, with reference to FIGS. 14 and 15. In this example, an error in the installation angle of each of the exposure heads $32_{12}$ and $32_{21}$ and a deviation of relative installation angles between the exposure heads $32_{12}$ and $32_{21}$ are considered, in addition to the deviation of the parallel relative positions between the exposure heads $32_{12}$ and $32_{21}$ considered in the example of pixel specification processing described with reference to FIGS. 10 to 13. In the example below, an effect caused by the error and the deviations is minimized, and the unevenness can further be reduced in resolution and density in the exposure surface.

In this example, the exposure apparatus 10 carries out 2-overlay exposure as in the embodiment described above. However, the predetermined installation angle of each of the exposure heads 30, that is, the installation angle θ of each of the DMD's 36, is set to an angle that is slightly larger than the ideal angle $θ_{ideal}$ satisfying Equation (1), such as 0.50 degree. This setting is adopted so that the actual installation angle of each of the exposure heads 30 does not become smaller than the ideal angle $θ_{ideal}$ regardless of a small error in the installation angle, although fine adjustment is difficult regarding the installation angle of each of the exposure heads 30. The exposure apparatus 10 has been initially adjusted so as to cause the installation angle of the exposure heads 30 (the DMD's 36) to be close to the installation angle θ in an adjustable range.

Figure 14:
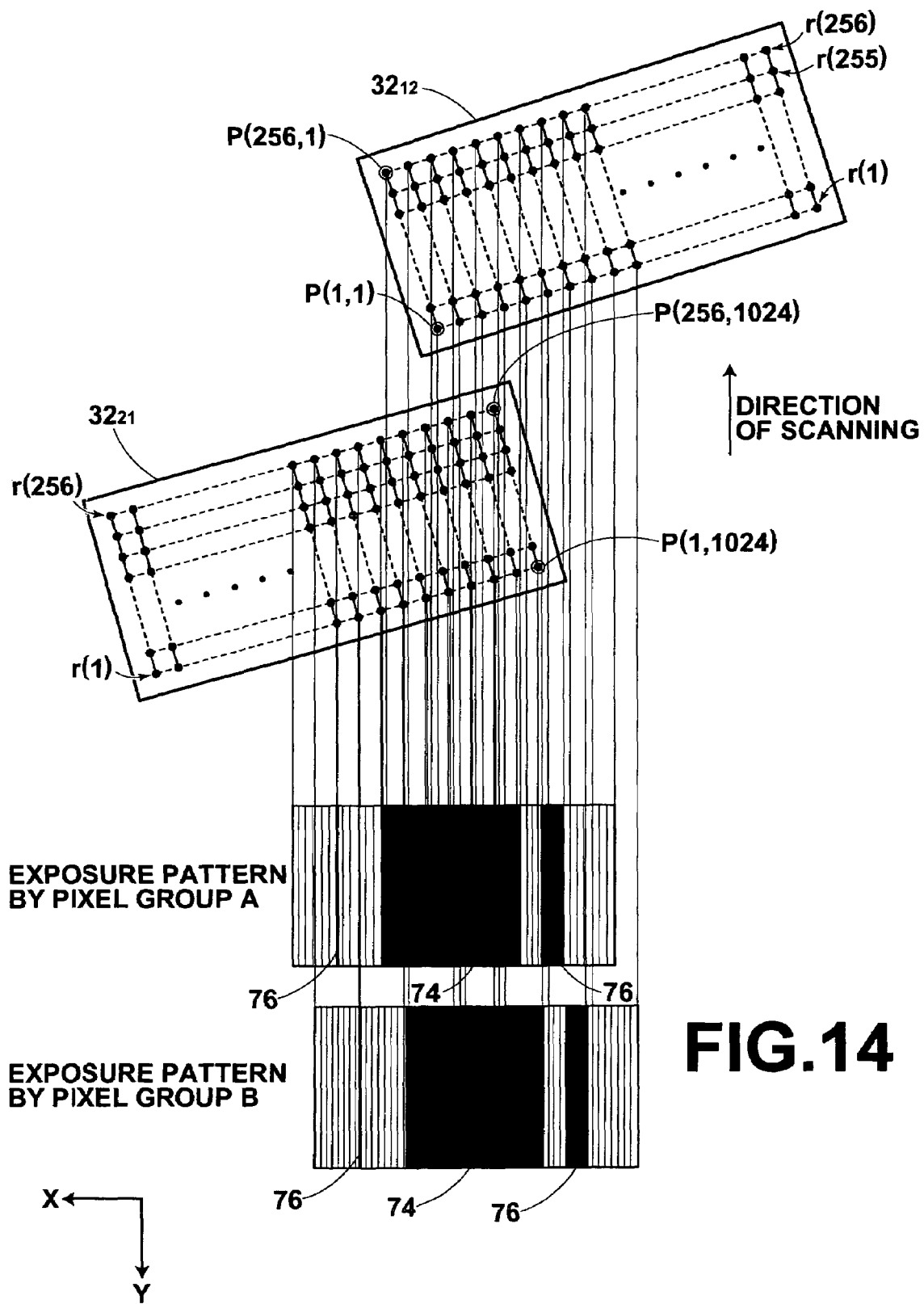
FIG. 14 shows an example of unevenness in a pattern in the exposure surface caused by an angle error and relative position error between the adjoining exposure heads.

FIG. 14 shows an example of unevenness in patterns on the exposure surface caused by the installation angle error and the deviation of the relative angles between two of the exposure heads 30 (such as the exposure heads $30_{12}$ and $30_{21}$) in the exposure apparatus 10 having been initially adjusted in the above manner, in addition to the deviation of the relative positions of the two exposure heads in the X axis direction.

In the example shown in FIG. 14, uneven density is observed in overexposure areas 74 compared to ideal 2-overlay exposure in both exposure patterns by the pixel groups A and B in the inter-head relay area between the exposure areas $32_{12}$ and $32_{21}$, due to the deviation of the relative positions between the exposure heads regarding the X axis direction, in the same manner as in FIG. 10. In addition, in the example shown in FIG. 14, uneven density is further observed in relay areas corresponding to both ends of pixel columns in the exposure patterns by the pixel groups A and B, as overexposure areas 76 compared to ideal 2-overlay exposure. The additional uneven density is caused by the installation angle θ of each of the exposure heads that is slightly larger than the ideal angle $θ_{ideal}$ satisfying Equation (1) and by a slight deviation of the actual installation angle from the angle θ due to difficulty in fine adjustment of the installation angle.

In this example, active pixel selection processing is carried out first in order to minimize the uneven density caused by the installation angle error and the deviation of the relative angles between the exposure heads $30_{12}$ and $30_{21}$. More specifically, an actual installation angle θ' of the pixel columns projected onto the exposure surface is identified for each of the exposure heads $30_{12}$ and $30_{21}$, by using the combination of the slit 28 and the photo detector. The processor connected to the photo detector selects the micro-mirrors to be practically used in exposure, based on the actual installation angle θ'. In order to find the actual installation angle θ', the combination of the slit 28 and the photo detector detects positions of the light spots P(1, 1) and P(256, 1) in the exposure area $32_{12}$ in FIG. 14 for the exposure head $30_{12}$ and positions of the light spots P(1, 1024) and P(256, 1024) in the exposure area $32_{21}$ for the exposure head $30_{21}$ in FIG. 14, for example. An angle between the lines connecting these light spots is then found by the processor.

Based on the actual installation angle θ' identified in the above manner, the processor connected to the photo detector finds, for each of the exposure heads $30_{12}$ and $30_{21}$, a natural number T closest to a value t satisfying Equation (4) below:

$$t \tan \theta' = N \quad (4)$$

The processor then identifies the micro-mirrors from the $(T+1)^{th}$ row to the $256^{th}$ row in each of the DMD 36 as the micro-mirrors that are not used for actual exposure. For example, in the case where T=254 and T=255 are respectively found for the exposure heads $30_{12}$ and $30_{21}$, the micro-mirrors corresponding to the light spots in hatched areas 78 and 80 in FIG. 15 are identified as the micro-mirrors that are not used for actual exposure. In this manner, the sum of the areas of overexposure and underexposure compared to the ideal 2-overlay exposure can be minimized in the areas other than the inter-head relay area between the exposure areas $32_{12}$ and $32_{21}$.

Instead of finding the natural number T closest to the value t, a natural number closest to t but larger than t may be found. In this case, the overexposure area is caused to be minimal while the underexposure area is caused to be absent in the areas other than the inter-head relay area between the exposure areas $32_{12}$ and $32_{21}$. Alternatively, a natural number closest to t but smaller than t may be found. In this case, the underexposure area is caused to be minimal while the overexposure area is caused to be absent in the areas other than the inter-head relay area between the exposure areas $32_{12}$ and $32_{21}$. In addition, the micro-mirrors that are not used in actual exposure may be identified by causing the number of the light spots in the overexposure area to be the same as the number of the light spots in the underexposure area in the areas other than the inter-head relay area.

Figure 15:
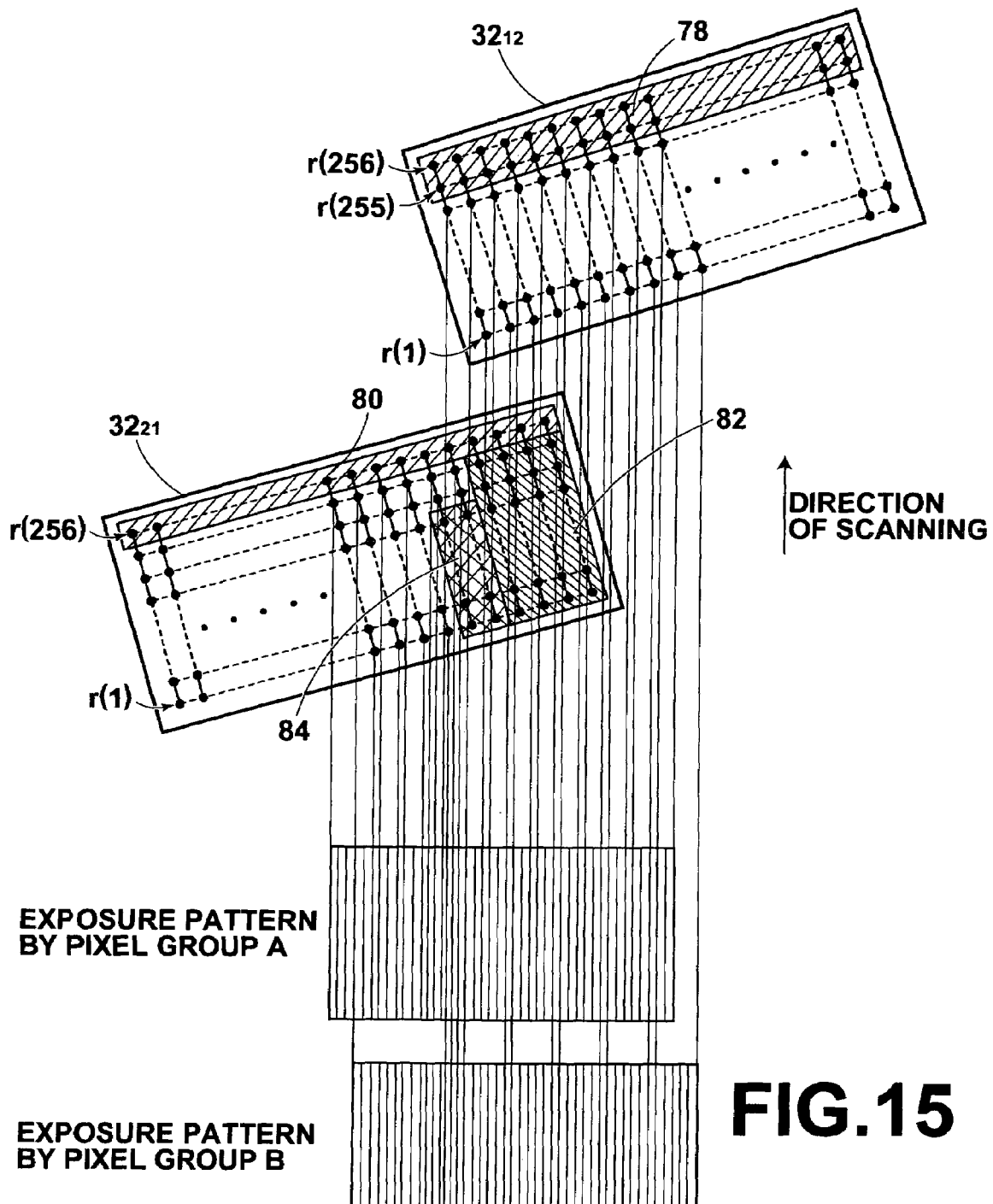
FIG. 15 shows a state of alleviated unevenness in the pattern in the exposure surface by operating only pixels selected in the example shown in FIG. 14.

Thereafter, the active pixel selection processing is carried out in the same manner as the description using FIGS. 10 to 13, regarding the micro-mirrors corresponding to the light spots other than the light spots comprising the hatched areas 78 and 80 in FIG. 15. The micro-mirrors corresponding to hatched and cross-hatched areas 82 and 84 in FIG. 15 are additionally identified as the micro-mirrors that are not used for actual exposure. The signal is sent to the micro-mirrors having been specified as the micro-mirrors that area not used for actual exposure, for setting the angle thereof to be in the OFF state. The specified micro-mirrors are not used for actual exposure.

According to the example described above, uniform 2-overlay exposure can be carried out by reducing the unevenness in resolution and density, in the entire image drawing surface including the inter-head relay areas and the remaining areas.

The embodiment of the image drawing apparatus of the present invention and the modification thereof described above in detail are merely examples, and various modifications can be made thereto within the scope of the present invention.

For example, in the above-described embodiment and the modification thereof, the combinations of the slits 28 and the single cell photo detectors are used as means for detecting the positions of the light spots in the exposure surface. However, means of any other form, such as two-dimensional detector, can be used therefor.

In the embodiment and the modification, the processors connected to the photo detectors are used for selecting the micro-mirrors to be practically used, based on the result of position detection by the combinations of the slits 28 and the photo detectors. However, reference exposure may be carried out by using all the usable micro-mirrors, for example.

Based on confirmation of unevenness in resolution and density by viewing a result of the reference exposure, for example, the micro-mirrors to be practically used may be specified manually by an operator, which is also within the scope of the present invention.

As another modification of the embodiment described above, reference exposure may be carried out by using the micro-mirrors comprising every (N−1) columns of pixels out of the usable micro-mirrors in the DMD 36 of each of the exposure heads 30, or by using the micro-mirrors comprising a group of pixel rows that are adjacent to each other and equivalent to 1/N of all the pixel rows. In this case, the micro-mirrors that are not used for actual exposure are selected from the micro-mirrors used in the reference exposure out of the micro-mirrors corresponding to the light spots in the inter-head relay areas, in order to realize a state that is close to ideal single exposure.

Figure 16:
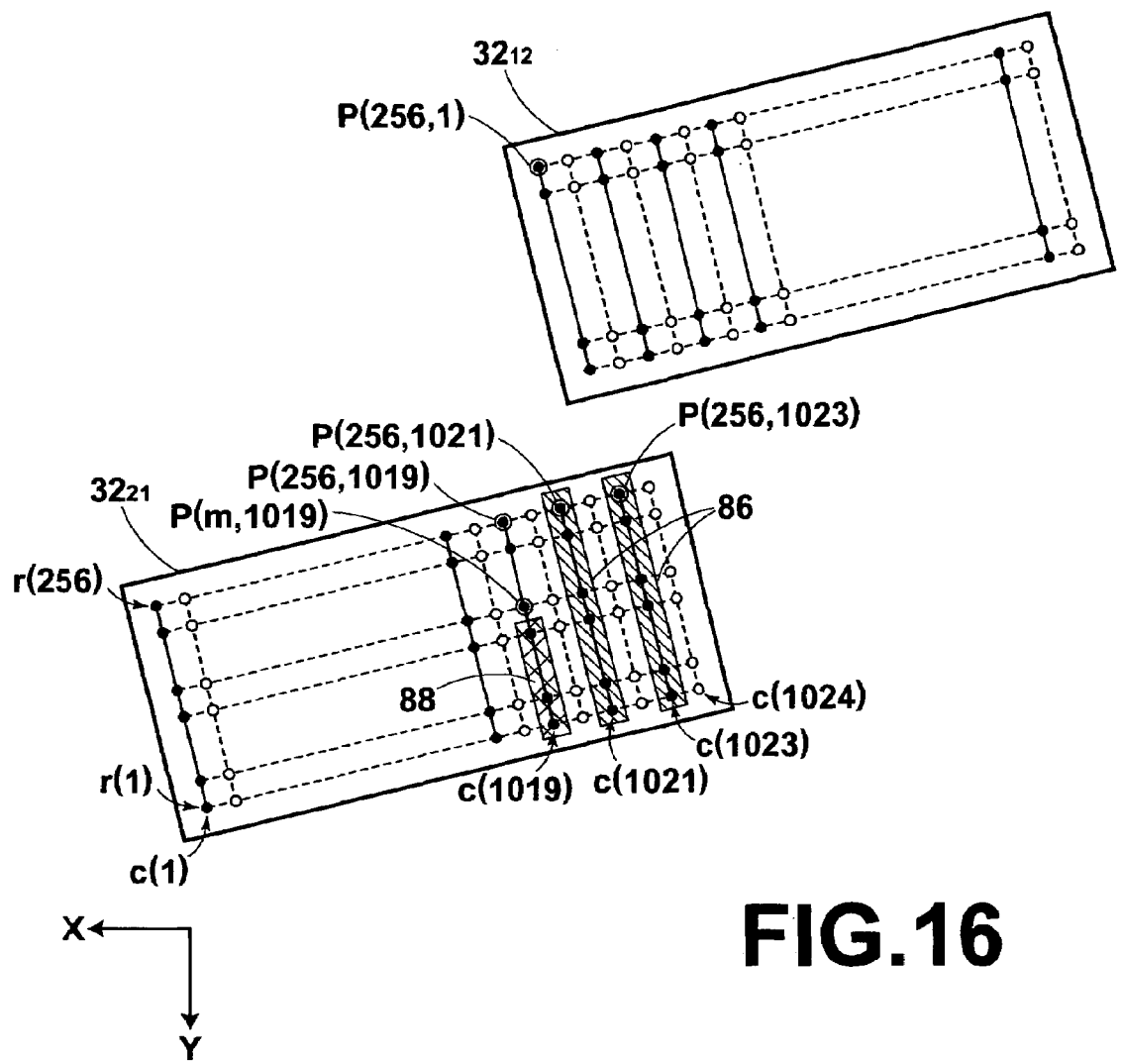
FIG. 16 shows a first example of reference exposure.

FIG. 16 shows an example of carrying out the reference exposure by using only the micro-mirrors comprising every (N−1) pixel columns. In this example, the actual exposure is 2-overlay exposure and thus N=2. The reference exposure is carried out first by using only the micro-mirrors corresponding to the columns of odd numbers shown by solid lines in FIG. 16 in two of the exposure heads (such as the exposure heads $30_{12}$ and $30_{21}$) that are adjacent to each other in the direction of X axis. A result of the reference exposure is then output. By confirming unevenness in resolution and density and inferring the actual installation angle while viewing the result of the reference exposure, an operator can specify the micro-mirrors to be used in actual exposure so that the actual exposure can be carried out with minimal unevenness in resolution and density in the inter-head relay areas. For example, the micro-mirrors other than the micro-mirrors corresponding to the columns of the light spots in hatched and cross-hatched areas 86 and 88 shown in FIG. 16 are specified as the micro-mirrors to be used in actual exposure out of the micro-mirrors comprising the columns of odd numbers. For the pixel columns of even numbers, the reference exposure is carried out separately in the same manner so that the micro-mirrors to be practically used can be determined. Alternatively, the same pattern as the columns of odd numbers maybe adopted therefor. By specifying the micro-mirrors to be used for actual exposure in the above manner, a state close to ideal 2-overlay exposure can be realized in the inter-head relay areas in actual exposure using the micro-mirrors of the columns of odd and even numbers. The result of the reference exposure may be analyzed not only by viewing but also by mechanical analysis.

Figure 17:
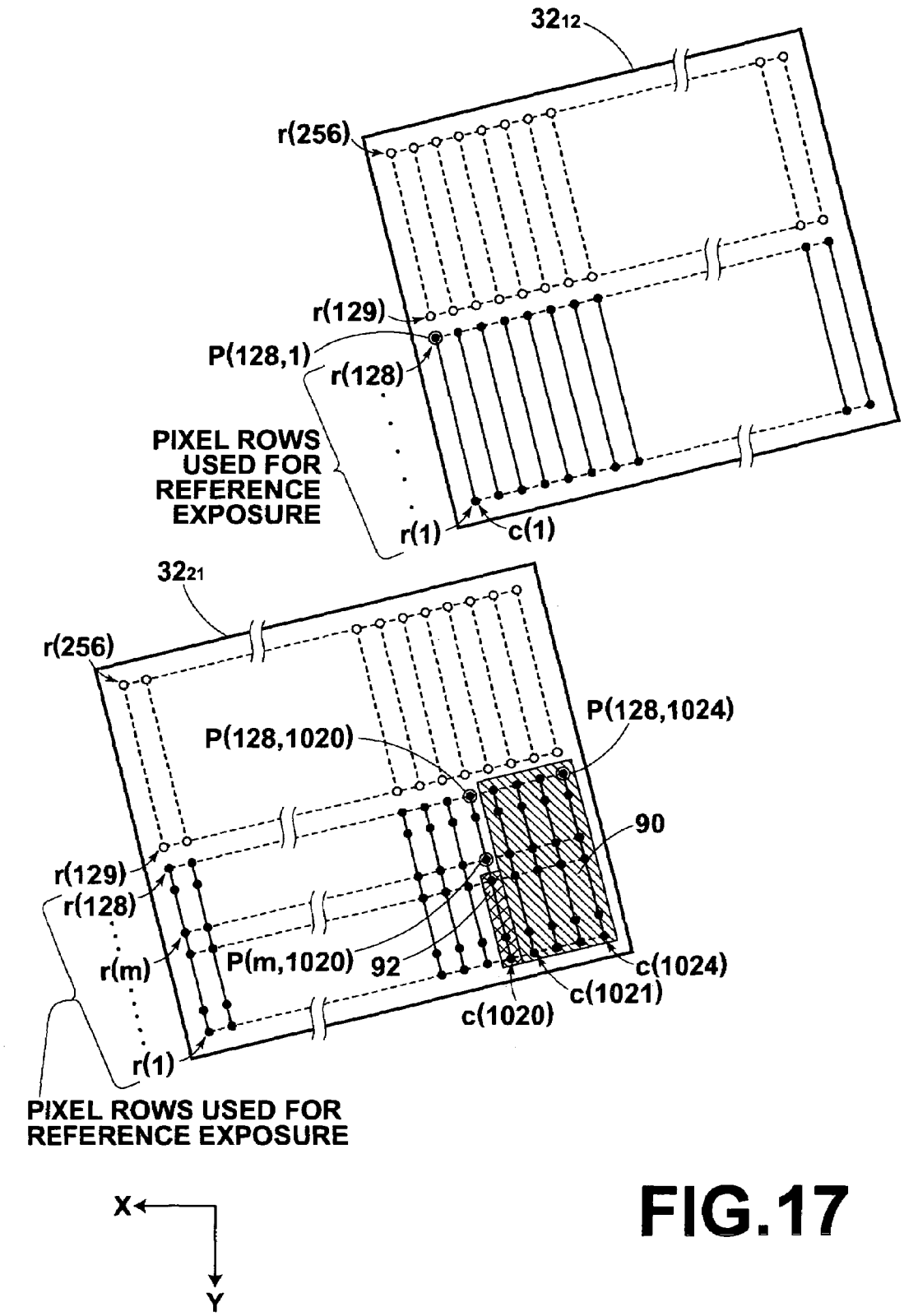
FIG. 17 shows a second example of reference exposure.

FIG. 17 shows an example of carrying out reference exposure by using only the micro-mirrors comprising the group of the adjoining pixel rows corresponding to 1/N of all the pixel rows, regarding two of the exposure heads (such as the exposure heads $30_{12}$ and $30_{21}$) that are adjacent to each other in the direction of X axis. In this example, 2-overlay exposure is carried out and thus N=2. The reference exposure is carried out by using only the micro-mirrors corresponding to the light spots from the first row to the $128^{th}$ (=256/2) row shown by solid lines in FIG. 17, and a result of the reference exposure is output. By confirming unevenness in resolution and density and inferring the actual installation angle while viewing the result of the reference exposure, an operator can specify the micro-mirrors to be used in actual exposure so that the actual exposure can be carried out with minimal unevenness in resolution and density in the inter-head relay areas. For example, the micro-mirrors other than the micro-mirrors corresponding to the light spots in hatched and cross-hatched areas 90 and 92 shown in FIG. 17 are specified as the micro-mirrors to be used in actual exposure out of the micro-mirrors from the first row to the $128^{th}$ row. For the micro-mirrors from the $129^{th}$ row to the $256^{th}$ row, the reference exposure may be carried out separately in the same manner to specify the micro-mirrors to be used. Alternatively, the same pattern as the micro-mirrors from the first row to the $128^{th}$ row may be adopted. By specifying the micro-mirrors to be used for actual exposure in the above manner, a state close to ideal 2-overlay exposure can be realized in the inter-head relay areas in actual exposure using the entire micro-mirrors. The result of the reference exposure may be analyzed not only by viewing but also by mechanical analysis.

In the above-described embodiment and the modifications thereof, the case of 2-overlay exposure in actual exposure has been described. However, any N-overlay exposure other than single exposure may be carried out. In order to further reduce residual unevenness in resolution and density in the two-dimensional pattern in the image drawing surface by the effect of filling, multiple-overlay exposure (2-overlay exposure or more) is preferably used. Especially, by using multiple-overlay exposure such as 3-overlay to 7-overlay exposure, exposure can be carried out in preferable balance where high resolution is maintained while unevenness in resolution and density is reduced.

It is preferable for the exposure apparatus in the embodiment and the modifications thereof to further have a mechanism for converting the image data so as to cause a size of a predetermined part in the two-dimensional pattern represented by the image data to match with a size of a corresponding part of the pattern to be generated by the micro-mirrors selected for actual exposure. By converting the image data in such a manner, the pattern can be formed on the exposure surface with high definition as desired.

In the exposure apparatus in the embodiment and the modifications described above, the DMD's that modulate the lights from the light sources for the respective pixels are used as the pixel arrays. However, light modulators other than DMD's such as a liquid crystal array or a light-source array (an LD array or an organic EL array, for example) may be used.

The exposure apparatus in the embodiment and the modifications may carry out continuous exposure by continuously moving the exposure heads. Alternatively, the exposure apparatus may carry out exposure by moving the exposure heads in a stepwise manner to a halt for exposure.

The active pixels in each of the inter-head relay areas may be selected by not using some of the pixels in either one of the corresponding exposure heads forming the inter-head relay area or by not using some of the pixels in both of the exposure heads.

The present invention is applied not only to the exposure apparatus and the exposure method but also to any image drawing apparatus and any image drawing method, as long as the image drawing apparatus and the image drawing method carry out N-overlay exposure (where N is a natural number) using a plurality of image drawing heads for generating a two-dimensional pattern represented by image data on an image drawing surface. For example, the present invention can be applied to an inkjet printer and an inkjet printing method. More specifically, a nozzle is generally formed in an inkjet recording head in an inkjet printer for propelling a droplet of ink, facing a recording medium (such as paper or an overhead projector sheet). In some inkjet printers, a plurality of such nozzles are formed in a grid-like shape, and recording heads are diagonally positioned to the direction of scanning for enabling an image to be recorded by N-overlay image drawing. If the present invention is applied to an inkjet printer adopting such two-dimensional arrangement and having deviation from an ideal state of relative positions and angles between the image drawing heads, some of the nozzles whose quantity can minimize the effect of the deviation are specified as the nozzles to be used practically. Therefore, uneven resolution and density can be reduced in inter-head relay areas in a recorded image.

Although the embodiment of the invention and modifications thereof have been described above in detail, the embodiment and the modifications are merely examples, and it is intended that the appended claims cover all such modifications as fall within the true spirit and scope of the invention.

What is claimed is:

1. An image drawing apparatus for forming a two-dimensional pattern represented by image data on an image drawing surface by N-overlay image drawing (where N refers to a natural number), the image drawing apparatus comprising:

image drawing heads each facing the image drawing surface and comprising a pixel array, the pixel arrays respectively having two-dimensionally arranged usable pixels and generating image drawing spots forming the two-dimensional pattern according to the image data, the image drawing heads being installed in such a manner that a direction of columns of the usable pixels forms a predetermined angle with a scanning direction of the image drawing heads;

moving means for moving the image drawing heads relatively to the image drawing surface in the scanning direction;

active pixel specification means for specifying, for each of the image drawing heads, active relay area pixels for realizing the N-overlay image drawing in an inter-head relay area in the image drawing surface among usable relay area pixels corresponding to the image drawing spots in the inter-head relay area out of the usable pixels; and setting change means for changing a setting in order to cause only the active relay area pixels to operate among the usable relay area pixels for each of the image drawing heads.

2. The image drawing apparatus according to claim 1, wherein the active pixel specification means further specifies active intra-area pixels out of the pixels other than the usable relay area pixels among the usable pixels for each of the image drawing heads, for realizing the N-overlay image drawing in areas other than the inter-head relay areas in the image drawing surface, and the setting change means changes the setting for each of the image drawing heads in order to cause only the active intra-area pixels to operate out of the pixels other than the usable relay area pixels among the usable pixels.

3. The image drawing apparatus according to claim 1, wherein the predetermined angle, represented by θ, of the image drawing heads satisfies:

$$sp \sin \theta \geq N\delta$$

where s refers to the number of pixels forming each of the columns of the usable pixels in each of the image drawing heads, p refers to a pitch of the usable pixels along a direction of the pixel columns, and δ refers to a pitch of the columns of the usable pixels projected onto a line perpendicular to the scanning direction.

4. The image drawing apparatus according to claim 1, wherein N is a natural number equal to or larger than 2.

5. The image drawing apparatus according to claim 1, wherein
the pixel arrays of the respective image drawing heads generate light spots as the image drawing spots, and
the active pixel specification section comprises:
position detection section which carries out detection of positions of the light spots forming the inter-head relay area in the image drawing surface among the light spots for each of the image drawing heads; and
selection section which selects the active relay area pixels for each of the image drawing heads in such a manner that a sum of a part wherein drawing is redundant and a part wherein drawing is deficient compared to the N-overlay image drawing in an ideal state becomes minimal in each of the inter-head relay areas in the image drawing surface, based on a result of the detection by the position detection section.

6. The image drawing apparatus according to claim 1, wherein
the pixel arrays of the respective image drawing heads generate light spots as the image drawing spots, and
the active pixel specification means comprises:
position detection means for carrying out detection of positions of the light spots forming the inter-head relay area in the image drawing surface among the light spots for each of the image drawing heads; and
selection means for selecting the active relay area pixels for each of the image drawing heads in such a manner that the number of the image drawing spots in a part where drawing is redundant becomes the same as the number of the image drawing spots in a part where drawing is deficient compared to the N-overlay image drawing in an ideal state in each of the inter-head relay areas in the image drawing surface, based on a result of the detection by the position detection means.

7. The image drawing apparatus according to claim 1, wherein
the pixel arrays of the respective image drawing heads generate light spots as the image drawing spots, and
the active pixel specification means comprises:
position detection means for carrying out detection of positions of the light spots forming the inter-head relay area in the image drawing surface among the light spots for each of the image drawing heads; and
selection means for selecting the active relay area pixels for each of the image drawing heads in such a manner that a part wherein drawing is redundant compared to the N-overlay image drawing in an ideal state becomes minimal in each of the inter-head relay areas while a part wherein drawing is deficient compared to the N-overlay image drawing in the ideal state is not observed, based on a result of the detection by the position detection means.

8. The image drawing apparatus according to claim 1, wherein
the pixel arrays of the respective image drawing heads generate light spots as the image drawing spots, and
the active pixel specification means comprises:
position detection means for carrying out detection of positions of the light spots forming the inter-head relay area in the image drawing surface among the image drawing spots for each of the image drawing heads; and
selection means for selecting the active relay area pixels for each of the image drawing heads in such a manner that a part wherein drawing is deficient compared to the N-overlay image drawing in an ideal state becomes minimal in each of the inter-head relay areas while a part wherein drawing is redundant compared to the N-overlay image drawing in the ideal state is not observed, based on a result of the detection by the position detection means.

9. The image drawing apparatus according to claim 4, further comprising reference image drawing means for carrying out reference image drawing by using only the pixels of every (N−1) columns among the usable relay area pixels for each of the image drawing heads, in order to specify the active relay area pixels by the active pixel specification means.

10. The image drawing apparatus according to claim 4, further comprising reference image drawing means for carrying out reference image drawing by using only the pixels comprising a group of adjoining pixel rows corresponding to 1/N of all the rows of the usable pixels among the usable relay area pixels for each of the image drawing heads, in order to specify the active relay area pixels by the active pixel specification means.

11. The image drawing apparatus according to claim 1, further comprising:
data conversion means for converting the image data so as to cause a size of a predetermined portion in each of the inter-head relay areas in the two-dimensional pattern represented by the image data to match with a size of a corresponding portion formed by the active relay area pixels that have been specified.

12. The image drawing apparatus according to claim 1, wherein the pixel arrays are spatial light modulators for modulating light from a light source according to the image data for each of the pixels.

13. An image drawing method using image drawing heads each comprising a pixel array and facing an image drawing surface, the pixel arrays respectively including two-dimensionally arranged usable pixels and generating image drawing spots according to image data for forming a two-dimensional pattern represented by the image data, the image drawing heads being installed in such a manner that a direction of columns of the usable pixels forms a predetermined angle with a direction of scanning by the image drawing heads, the image drawing method comprising the steps of:
specifying, for each of the image drawing heads, active relay area pixels for realizing N-overlay image drawing (where N is a natural number) in an inter-head relay area in the image drawing surface, among usable relay area pixels corresponding to the image drawing spots in the inter-head relay area out of the usable pixels;
changing a setting of the image drawing heads so that only the active relay area pixels to operate out of the usable relay area pixels for each of the image drawing heads; and
forming the two-dimensional pattern on the image drawing surface by causing the image drawing heads to operate with movement relative to the image drawing surface in the scanning direction.

* * * * *